United States Patent
Kapur et al.

(10) Patent No.: US 10,478,819 B2
(45) Date of Patent: Nov. 19, 2019

(54) SORTING PARTICLES IN A MICROFLUIDIC DEVICE

(71) Applicant: The General Hospital Corporation, Boston, MA (US)

(72) Inventors: Ravi Kapur, Sharon, MA (US); Kyle C. Smith, Cambridge, MA (US); Mehmet Toner, Charlestown, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 16/112,275

(22) Filed: Aug. 24, 2018

(65) Prior Publication Data

US 2018/0361384 A1     Dec. 20, 2018

Related U.S. Application Data

(60) Continuation of application No. 15/891,579, filed on Feb. 8, 2018, which is a division of application No.
(Continued)

(51) Int. Cl.
*G01N 1/18*      (2006.01)
*G01N 1/00*      (2006.01)
(Continued)

(52) U.S. Cl.
CPC ........ *B01L 3/502761* (2013.01); *A61K 35/28* (2013.01); *B01L 3/502715* (2013.01);
(Continued)

(58) Field of Classification Search
CPC ............ G01N 1/18; G01N 1/00; G01N 15/10; G01N 27/327; G01N 15/02
(Continued)

(56) References Cited

U.S. PATENT DOCUMENTS

| 5,968,820 A | 10/1999 | Zborowski et al. |
| 6,540,896 B1 | 4/2003 | Manz et al. |

(Continued)

FOREIGN PATENT DOCUMENTS

| CN | 101678356 | 3/2010 |
| CN | 101765762 A | 6/2010 |

(Continued)

OTHER PUBLICATIONS

Augustsson et al., "Microfluidic, Label-Free Enrichment of Prostate Cancer Cells in Blood Based on Acoustophoresis," Anal. Chem., 84(18):7954-7965, Sep. 2012.
(Continued)

*Primary Examiner* — Brian J. Sines
(74) *Attorney, Agent, or Firm* — Fish & Richardson P.C.

(57) ABSTRACT

A microfluidic device includes a particle sorting region having a first, second and third microfluidic channels, a first array of islands separating the first microfluidic channel from the second microfluidic channel, and a second array of islands separating the first microfluidic channel from the third microfluidic channel, in which the island arrays and the microfluidic channels are arranged so that a first fluid is extracted from the first microfluidic channel into the second microfluidic channel and a second fluid is extracted from the third microfluidic channel into the first microfluidic channel, and so that particles are transferred from the first fluid sample into the second fluid sample within the first microfluidic channel.

14 Claims, 12 Drawing Sheets

Related U.S. Application Data

14/931,223, filed on Nov. 3, 2015, now Pat. No. 9,895,694.

(60) Provisional application No. 62/074,213, filed on Nov. 3, 2014, provisional application No. 62/074,315, filed on Nov. 3, 2014.

(51) Int. Cl.
G01N 15/10 (2006.01)
G01N 15/02 (2006.01)
B01L 3/00 (2006.01)
G01N 1/40 (2006.01)
G01N 15/14 (2006.01)
A61K 35/28 (2015.01)
G01N 15/06 (2006.01)
G01N 15/00 (2006.01)

(52) U.S. Cl.
CPC ... *B01L 3/502746* (2013.01); *B01L 3/502753* (2013.01); *G01N 1/4077* (2013.01); *G01N 15/0255* (2013.01); *G01N 15/0618* (2013.01); *G01N 15/1484* (2013.01); *B01L 3/502776* (2013.01); *B01L 2200/0631* (2013.01); *B01L 2200/0647* (2013.01); *B01L 2200/0652* (2013.01); *B01L 2200/0668* (2013.01); *B01L 2200/0684* (2013.01); *B01L 2200/12* (2013.01); *B01L 2300/0681* (2013.01); *B01L 2300/0877* (2013.01); *B01L 2300/185* (2013.01); *B01L 2400/043* (2013.01); *B01L 2400/0409* (2013.01); *B01L 2400/0415* (2013.01); *B01L 2400/0436* (2013.01); *B01L 2400/0457* (2013.01); *B01L 2400/0487* (2013.01); *B01L 2400/082* (2013.01); *G01N 2001/4088* (2013.01); *G01N 2015/0053* (2013.01); *G01N 2015/0065* (2013.01); *G01N 2015/0288* (2013.01); *G01N 2015/149* (2013.01); *G01N 2015/1486* (2013.01); *G01N 2015/1493* (2013.01)

(58) Field of Classification Search
USPC ...... 436/43, 63, 174, 175, 177, 180; 422/50, 422/68.1, 81, 82, 502, 503, 504
See application file for complete search history.

(56) References Cited

U.S. PATENT DOCUMENTS

| | | | |
|---|---|---|---|
| 6,632,652 B1 | 10/2003 | Austin | |
| 6,767,706 B2 | 7/2004 | Quake et al. | |
| 7,560,267 B2 | 7/2009 | Yang et al. | |
| 7,641,865 B2 | 1/2010 | Tonkovich et al. | |
| 7,837,040 B2 | 11/2010 | Ward et al. | |
| 8,021,614 B2 | 9/2011 | Huang et al. | |
| 8,186,913 B2 | 5/2012 | Toner et al. | |
| 8,906,322 B2 | 12/2014 | Huang et al. | |
| 2002/0187503 A1 | 12/2002 | Harrold | |
| 2003/0092029 A1 | 5/2003 | Josephson et al. | |
| 2003/0124194 A1 | 7/2003 | Gaw et al. | |
| 2003/0175944 A1 | 9/2003 | Yang et al. | |
| 2003/0226806 A1 | 12/2003 | Young et al. | |
| 2004/0033515 A1 | 2/2004 | Cao et al. | |
| 2004/0053403 A1 | 3/2004 | Jedrzejewski et al. | |
| 2004/0126890 A1 | 7/2004 | Gjerde | |
| 2004/0144651 A1 | 7/2004 | Huang et al. | |
| 2005/0109716 A1 | 5/2005 | Leach et al. | |
| 2006/0011480 A1 | 1/2006 | Sano et al. | |
| 2006/0068490 A1 | 3/2006 | Tang | |
| 2006/0078888 A1 | 4/2006 | Griffiths et al. | |
| 2006/0160243 A1 | 7/2006 | Tang et al. | |
| 2006/0269965 A1 | 11/2006 | Josephson et al. | |
| 2007/0026381 A1* | 2/2007 | Huang | B01L 3/502746 435/4 |
| 2007/0026419 A1 | 2/2007 | Fuchs et al. | |
| 2007/0059781 A1 | 3/2007 | Kapur et al. | |
| 2007/0099207 A1 | 5/2007 | Fuchs et al. | |
| 2007/0196820 A1 | 8/2007 | Kapur et al. | |
| 2008/0023399 A1* | 1/2008 | Inglis | B01L 3/502753 210/649 |
| 2009/0032449 A1 | 2/2009 | Mueth et al. | |
| 2009/0269767 A1 | 10/2009 | Soderlund et al. | |
| 2010/0006479 A1 | 1/2010 | Reichenbach | |
| 2010/0059414 A1* | 3/2010 | Sturm | G01N 27/44791 209/155 |
| 2011/0091987 A1 | 4/2011 | Weissleder et al. | |
| 2012/0037544 A1* | 2/2012 | Lane | B01L 3/502753 209/17 |
| 2012/0258459 A1 | 10/2012 | Huang | |
| 2013/0079251 A1* | 3/2013 | Boles | C12M 45/09 506/26 |
| 2013/0086980 A1* | 4/2013 | Gadini | B01L 3/502753 73/61.71 |
| 2013/0121895 A1 | 5/2013 | Tang et al. | |
| 2013/0168298 A1 | 7/2013 | Huang et al. | |
| 2013/0228530 A1 | 9/2013 | Di Carlo et al. | |
| 2014/0030788 A1 | 1/2014 | Chen et al. | |
| 2014/0093867 A1 | 4/2014 | Burke et al. | |
| 2014/0227777 A1 | 8/2014 | Choi et al. | |
| 2014/0248621 A1 | 9/2014 | Collins | |
| 2014/0342375 A1* | 11/2014 | Grisham | B01L 3/502753 435/7.24 |
| 2015/0202356 A1 | 7/2015 | Gifford | |
| 2016/0047735 A1 | 2/2016 | Grisham et al. | |
| 2016/0139012 A1* | 5/2016 | D'Silva | G01N 33/5094 424/93.7 |
| 2017/0209864 A1* | 7/2017 | Grisham | B01L 3/502746 |
| 2017/0225166 A1* | 8/2017 | Toner | G01N 33/54366 |

FOREIGN PATENT DOCUMENTS

| | | |
|---|---|---|
| CN | 102791616 A | 11/2012 |
| JP | 2004-170396 | 6/2004 |
| JP | 2007-196219 | 8/2007 |
| JP | 2013-515599 | 5/2013 |
| WO | 2000/061191 | 10/2000 |
| WO | WO 2004/037374 | 5/2004 |
| WO | 2004/074814 | 9/2004 |
| WO | WO 2005/086703 | 9/2005 |
| WO | WO 2006/108087 | 10/2006 |
| WO | WO 2010/123594 | 10/2010 |
| WO | WO 2011/132164 | 10/2011 |
| WO | WO 2012/067985 | 5/2012 |
| WO | 2014/004577 | 1/2014 |
| WO | WO 2014/107240 | 7/2014 |
| WO | 2015/116990 | 8/2015 |

OTHER PUBLICATIONS

Burke et al., "High-throughput particle separation and concentration using spiral inertial filtration," Biomicrofluidics 8, 024105 (2014), 18 pages.

D'Avino et al., "Single line particle focusing induced by viscoelasticity of the suspending liquid: theory, experiments and simulations to design a micropipe flow-focuser," Lab Chip, 12(9):1638-1645, Feb. 2012.

David W. Inglis, Efficient Microfluidic Particle Separation Arrays, 013510-1 to 013510-3, Jan. 9, 2009, American Institute of Physics, Published Online.

Del Giudice et al., "Particle alignment in a viscoelastic liquid flowing in a square-shaped microchannel," Lab Chip, 2013, 13, pp. 4263-4271, Aug. 2013.

Di Carlo et al., "Continuous inertial focusing, ordering, and separation of particles in microchannels," Proc. Natl. Acad. Sci. U.S.A., 104(48):18892-18897, Nov. 2007.

Di Carlo et al., "Particle segregation and dynamics in confined flows," Phys. Rev. Lett., 102(9):094503, Mar. 2009.

(56) References Cited

OTHER PUBLICATIONS

Di Carlo, "Inertial microfluidics," Lab Chip, 9(21):3038-3046, Aug. 2009.
Extended European Search Report in Application No. 15856423.7, dated Apr. 20, 2018, 8 pages.
Extended European Search Report in Application No. 15856708.1, dated May 16, 2018, 9 pages.
Extended European Search Report in Application No. 15856773.5, dated Apr. 20, 2018, 9 pages.
Gifford et al., "Controlled Incremental Filtration: A simplified approach to design and fabrication of high-throughput microfluidic devices for selective enrichment of particles," Lab Chip, DOI: 10.1039/C4LC00785A, Sep. 2014, 30 pages.
International Preliminary Report on Patentability in International Application No. PCT/US2015/058841, dated May 9, 2017.
International Preliminary Report on Patentability in International Application No. PCT/US2015/058834, dated May 9, 2017.
International Preliminary Report on Patentability in International Application No. PCT/US2015/058785, dated May 9, 2017.
International Search Report and Written Opinion in International Application No. PCT/US2015/058834, dated Feb. 17, 2016, 13 pages.
International Search Report and Written Opinion in International Application No. PCT/US2015/058785, dated Feb. 16, 2016, 10 pages.
International Search Report in International Application No. PCT/US2015/058841, dated Feb. 23, 2016, 5 pages.
Kang et al., "DNA-based highly tunable particle focuser," Nature Communications, 4:2567, Oct. 2013, 8 pages.
Lee et al., "Dynamic self-assembly and control of microfluidic particle crystals," Proceedings of the National Academy of Sciences, 107(52):22413-22418, Nov. 2010.
Lee et al., "Multiplex Particle Focusing via Hydrodynamic Force in Viscoelastic Fluids," Scientific Reports, 3:3258, Nov. 2013, 8 pages.
Lim et al., "Inertio-elastic focusing of bioparticles in microchannels at high throughput," Nature Communications, (5:4120), pp. 1-9, Jun. 2014.
Loutherback, "Microfluidic Devices for High Throughput Cell Sorting and Chemical Treatment," Dissertation, Nov. 2011.
Lubbersen et al., "High throughput particle separation with a mirrored deterministic ratchet design", Chemical Engineering and Processing 77 (2014) 42-49.
Lubbersen et al., "Visualization of inertial flow in deterministic ratchets", Separation and Purification Technology 109 (2013) 33-39.
Martel and Toner, "Inertial Focusing in Microfluidics," Annual Review of Biomedical Engineering, 16:371-396, Jul. 2014.
Martel and Toner, "Particle Focusing in Curved Microfluidic Channels," Scientific Reports, 3(3340): Nov. 1-8, 2013.
Office Action in U.S. Appl. No. 14/931,223, dated May 19, 2017, 15 pages.
Office Action in U.S. Appl. No. 14/931,421, dated May 19, 2017, 19 pages.
Office Action in U.S. Appl. No. 14/931,421, dated Oct. 4, 2017, 15 pages.
Peterson et al., "Bacterial Cell Surface Damage Due to Centrifugal Compaction," Applied and Environmental Microbiology, 78(1):120-125, Jan. 2012.
Shen et al., "High-throughput rare cell separation from blood samples using steric hindrance and inertial microfluidics," Lab Chip, 2014, DOI: 10.1039/C3LC51384J, Mar. 2014, 15 pages.
Tanyeri et al., "A microfluidic-based hydrodynamic trap: Design and implementation," Lab Chip, 11(10):1786-1794, May 2011.
Written Opinion in International Application No. PCT/US2015/058841, dated Feb. 23, 2016, 14 pages.
Yang et al., "Sheathless elasto-inertial particle focusing and continuous separation in a straight rectangular microchannel," Lab Chip, 11(2):266-273, Jan. 2011.
Office Action in Japanese Application No. 2017-523990, dated Dec. 18, 2018, 10 pages (with English translation).
Office Action in Indian Application No. 201737018682, dated May 22, 2019, 6 pages.
Office Action in Japanese Application No. 2017-523990, dated Jun. 7, 2019, 7 pages (with English translation).
Office Action in Chinese Application No. 201580071263.4, dated Apr. 2, 2019, 34 pages (with English tmnslation).
Office Action in Chinese Application No. 201580069630.7, dated Apr. 2, 2019, 23 pages (with English tmnslation).
Office Action in Chinese Application No. 201580071415.0, dated Apr. 2, 2019, 26 pages (with English tmnslation).

\* cited by examiner

SORTING PARTICLES IN A MICROFLUIDIC DEVICE

CROSS-REFERENCE TO RELATED APPLICATIONS

This application is a continuation of Ser. No. 15/891,579, filed on Feb. 8, 2018, which is a divisional of U.S. patent application Ser. No. 14/931,223, filed on Nov. 3, 2015, which claims the benefit of U.S. Provisional Patent Application No. 62/074,213, filed Nov. 3, 2014 and U.S. Provisional Patent Application No. 62/074,315, filed Nov. 3, 2014, each of which is incorporated herein by reference in its entirety.

TECHNICAL FIELD

The present disclosure relates to particle sorting across microfluidic streamlines.

BACKGROUND

Particle separation and filtration have been used in numerous applications across industries and fields. Examples of such applications include chemical process and fermentation filtration, water purification/wastewater treatment, sorting and filtering components of blood, concentrating colloid solutions, and purifying and concentrating environmental samples. Various macro-scale techniques have been developed for use in these applications including methods such as centrifugation and filter-based techniques. Typically, such techniques require systems that are large, bulky, and expensive and have complex moving components.

In certain cases, micro-scale techniques offer advantages over macro-scale techniques, in that scaling down allows the use of unique hydrodynamic effects for particle sorting and filtration, and thus eliminates the need for large systems with complex moving components. Moreover, micro-scale techniques offer the possibility of portable devices capable of performing sorting and filtration at much lower cost than larger macro-scale systems. However, typical micro-scale sorting and filtration devices may be limited in the amount of fluid they can handle over a specified period of time (i.e., low throughput), potentially placing such devices at a disadvantage to their macro-scale counterparts.

SUMMARY

The present disclosure is based, at least in part, on the discovery that if one carefully controls the geometries and dimensions of microfluidic devices one can combine both fluid extraction and inertial lift forces for the purpose of sorting and/or shifting particles within or among fluids. In particular, through fluid extraction and inertial lift forces, the microfluidic devices disclosed herein may be used to transfer fluids to and across different fluidic channels of the device, without an accompanying shift of particles, such that the particles may be indirectly transferred to another fluid. Alternatively, or in addition, the techniques disclosed herein can be used in certain implementations to manipulate not only the transfer of fluids across micro-channels but also the position of particles suspended within a fluid sample through the shifting of the particles across fluid streamlines.

For instance, a first fluid containing particles may be introduced into a first microfluidic channel having arrays of rigid island structures separating the channel from two adjacent microfluidic channels. Fluid is extracted from the first microfluidic channel into one of the adjacent microfluidic channels through gaps between island structures in a first array, so that the particles are drawn nearer to the island structures. As the particles reach nearer to the island structures, the particles experience an inertial lift force away from the direction of fluid extraction such that the particles remain in the first channel. At the same time, a second fluid from the other adjacent microfluidic channel passes into the first microfluidic channel through gaps between island structures in a second array. As the fluid from the other adjacent channel enters the first channel, the particles within the first channel cross fluid streamlines, resulting in the shift of the particles from the first fluid to the second fluid. If the amount of first fluid that is extracted from the first channel at each gap of the first array equals the amount of second fluid that enters the first channel at each gap of the second array, then a constant particle concentration can be maintained.

In addition to shifting particles between fluids, the combination of fluid extraction and inertial lift force enables a number of different ways of manipulating fluids and particles. For example, in some implementations, different types of particles may be separated into different channels, e.g., larger particles may be separated from smaller particles, to achieve micro-scale sorting of particles and/or filtering of particles from fluids. Alternatively, in some implementations, the combination of fluid extraction and inertial lift may be used to mix different types of particles. In some cases, both particle separation and shifting between fluids (or particle mixing and shifting between fluids) may be performed together. In another example, the combined fluid extraction and inertial lift forces may be used to focus particles to desired positions within a microfluidic channel. These and other applications may be scaled over large numbers of microfluidic channels to achieve high throughput sorting/filtering of fluids in systems with low device fabrication costs.

In general, in one aspect, the subject matter of the present disclosure may be embodied in a microfluidic device including a particle sorting region having a first microfluidic channel, a second microfluidic channel extending along the first microfluidic channel, and a first array of islands separating the first microfluidic channel from the second microfluidic channel, in which each island in the array is separated from an adjacent island in the array by an opening that fluidly couples the first microfluidic channel to the second microfluidic channel, and in which the first microfluidic channel, the second microfluidic channel, and the first array of islands are arranged so that a fluidic resistance of the first microfluidic channel relative to a fluidic resistance of the second microfluidic channel changes along a longitudinal section of the particle sorting region, such that a portion of fluid from a fluid sample in the first microfluidic channel or the second microfluidic channel passes through the opening.

In general, in another aspect, the subject matter of the present disclosure may be embodied in a microfluidic device that includes: a particle sorting region having a first microfluidic channel, a second microfluidic channel extending along a first side of the first microfluidic channel, a first array of islands separating the first microfluidic channel from the second microfluidic channel, in which each island in the first array is separated from an adjacent island in the first array by an opening that fluidly couples the first microfluidic channel to the second microfluidic channel, a third microfluidic channel extending along a second side of the first microfluidic channel, the second side being opposite to the first side of the first microfluidic channel, a second array of islands separating the first microfluidic channel from the third microfluidic channel, in which each island in the second array is separated from an adjacent island in the second array by an opening that fluidly couples the first microfluidic channel to the third microfluidic channel, in which the first microfluidic channel, the second microfluidic channel, and the first array of islands are arranged so that the fluidic resistance of the second microfluidic channel decreases along a longitudinal direction of the particle sorting region relative to the fluidic resistance of the first microfluidic channel, such that, during operation of the microfluidic device, a portion of fluid from a fluid sample in the first microfluidic channel passes through the first array into the second microfluidic channel, and in which the first microfluidic channel, the third microfluidic channel and the second array of islands are arranged so that a fluidic resistance of the third microfluidic channel increases along the longitudinal direction of the particle sorting region relative to the fluidic resistance of the first microfluidic channel, such that, during operation of the microfluidic device, a portion of fluid from a fluid sample in the third microfluidic channel passes through the second array into the first microfluidic channel.

Implementations of the devices may have one or more of the following features. For example, in some implementations, the changing fluidic resistance is a function of an increasing cross-sectional area of the first microfluidic channel or the second microfluidic channel along a longitudinal direction of the particle sorting region. For instance, a width of one of the first microfluidic channel or the second microfluidic channel may increase along the longitudinal direction. A width of the other of the first microfluidic channel or the second microfluidic channel may be substantially constant along the longitudinal direction. Alternatively, a width of the other of the first microfluidic channel or the second microfluidic channel may decrease along the longitudinal direction.

In some implementations, the decrease in the fluidic resistance of the second microfluidic channel relative to the fluidic resistance of the first microfluidic channel is a function of an increasing cross-sectional area of the second microfluidic channel along the longitudinal direction of the particle sorting region. A width of the first microfluidic channel can be substantially constant along the longitudinal direction.

In some implementations, a cross-sectional area of the gaps between islands in the first array increases along the longitudinal direction, the cross-sectional area of each gap in the first array being defined along a plane that is transverse to fluid flow through the gap. The increase in the fluidic resistance of the third microfluidic channel relative to the fluidic resistance of the first microfluidic channel can be a function of a decreasing cross-sectional area of the third microfluidic channel along the longitudinal direction of the particle sorting region. A width of the first microfluidic channel can be substantially constant along the longitudinal direction.

In some implementations, a cross-sectional area of the gaps between islands in the second array increases along the longitudinal direction, the cross-sectional area of each gap in the second array being defined along a plane that is transverse to fluid flow through the gap.

In some implementations, the microfluidic devices further include: a first inlet channel; and a second inlet channel, in which each of the first inlet channel and the second inlet channel is fluidly coupled to the particle sorting region.

In some implementations, a size of each opening in the first array is greater than a size of a previous opening in the array along the longitudinal section.

In some implementations, the particle and fluid shifting region further includes a third microfluidic channel extending along the first microfluidic channel, and a second array of islands separating the first microfluidic channel and the third microfluidic channel, in which the first microfluidic channel is located between the second and third microfluidic channels. The changing relative fluidic resistance may be a function of an increasing cross-sectional area of the second microfluidic channel or the third microfluidic channel along a longitudinal direction of the particle sorting region. For instance, a width of one of the second microfluidic channel or the third microfluidic channel may increase along the longitudinal direction. Alternatively, a width of the other one of the second microfluidic channel or the third microfluidic channel may decrease along the longitudinal direction. In some cases, a width of the first microfluidic channel may be substantially constant along the longitudinal direction. The changing relative fluidic resistance may be a function of an increasing cross-sectional area of the second microfluidic channel and the third microfluidic channel along a longitudinal direction of the particle sorting region.

In some implementations, the devices further include a first inlet channel and a second inlet channel, in which each of the first inlet channel and the second inlet channel is fluidly coupled to the particle sorting region.

In another aspect, the subject matter of the present disclosure may be embodied in methods of sorting particles in a fluid sample, in which the methods include flowing a first fluid sample containing a group of a first type of particle into a particle sorting region of a microfluidic device, in which the particle sorting region includes a first microfluidic channel, a second microfluidic channel extending along the first microfluidic channel, and a first array of islands separating the first microfluidic channel from the second microfluidic channel. The methods may further include flowing a second fluid sample into the particle sorting region, in which a fluidic resistance between the first microfluidic channel and the second microfluidic channel changes along a longitudinal section of the particle sorting region such that a portion of the first fluid sample passes from the first microfluidic channel into the second microfluidic channel through openings between islands in the first array, and in which the first microfluidic channel, the second microfluidic channel and the first array of islands are further arranged to generate inertial lift forces that substantially prevent the group of the first type of particle from propagating with the siphoned fluid portion through the openings of the first array.

In another aspect, the subject matter of the present disclosure may be embodied in methods of shifting particles between fluid samples in a microfluidic device, the methods including: flowing a first fluid sample containing multiple first types of particle into a particle sorting region of the microfluidic device, in which the particle sorting region includes a first microfluidic channel, a second microfluidic channel extending along a first side of the first microfluidic channel, a first array of islands separating the first microfluidic channel from the second microfluidic channel, a third microfluidic channel extending along a second side of the first microfluidic channel, and a second array of islands separating the first microfluidic channel from the third microfluidic channel, the second side being opposite to the first side of the first microfluidic channel, each island in the first array being separated from an adjacent island in the first array by an opening that fluidly couples the first microfluidic channel to the second microfluidic channel, and each island in the second array being separated from an adjacent island in the second array by an opening that fluidly couples the first microfluidic channel to the third microfluidic channel; and flowing a second fluid sample into the particle sorting region, in which a fluidic resistance of the second microfluidic channel changes relative to a fluidic resistance of the first microfluidic channel along a longitudinal direction of the particle sorting region such that a portion of the first fluid sample passes from the first microfluidic channel into the second microfluidic channel through openings between islands in the first array, a fluidic resistance of the third microfluidic channel changes relative to the fluidic resistance of the first microfluidic channel along the longitudinal direction of the particle sorting region such that a portion of the second fluid sample passes from the third microfluidic channel into the first microfluidic channel through openings between islands in the second array, and the first microfluidic channel, the second microfluidic channel and the first array of islands are further arranged to generate inertial lift forces that substantially prevent the multiple first types of particle from propagating with the portion of the first fluid sample that passes through the openings of the first array.

Implementations of the methods may have one or more of the following features. For example, in some implementations, both the first fluid sample and the second fluid sample are delivered to the first microfluidic channel. The second fluid sample may continuously flow through the first microfluidic channel without being substantially siphoned through the openings into the second microfluidic channel. The inertial lift forces may shift the group of the first type of particles across fluid streamlines so that the group of the first type of particles is transferred to the second fluid sample.

In some implementations, the first fluid sample is delivered to the first microfluidic channel and the second fluid sample is delivered to the third microfluidic channel.

In some implementations, the inertial lift forces shift the multiple first types of particle across fluid streamlines so that the multiple first types of particle are transferred from the first fluid sample to the second fluid sample within the first microfluidic channel.

In some implementations, the first fluid sample includes multiple second types of particle, in which the multiple second types of particle propagate with the fluid portion of the first fluid sample that passes into the second microfluidic channel. The first type of particle can be larger than the second type of particle.

In some implementations, the first fluid sample includes a different fluid than the second fluid sample.

In some implementations, the amount of the first fluid sample that passes from the first microfluidic channel into the second microfluidic channel is substantially the same as the amount of the second fluid sample that passes from the third microfluidic channel into the first microfluidic channel so that a concentration of the first type of particle within the first microfluidic channel remains substantially constant.

In some implementations, the change in the fluidic resistance of the second microfluidic channel relative to the fluidic resistance of the first microfluidic channel includes an increase in a cross-sectional area of the second microfluidic channel along the longitudinal direction.

In some implementations, the change in the fluidic resistance of the third microfluidic channel relative to the fluidic resistance of the microfluidic channel includes an increase in a cross-sectional area of the third microfluidic channel along the longitudinal direction.

In some implementations, the first fluid sample includes multiple second types of particle, and the multiple second types of particle propagate with the fluid portion of the first fluid sample that passes into the second microfluidic channel. The first type of particle can be larger than the second type of particle.

The first type of particle may have an average diameter between about 1 μm and about 100 μm.

In another aspect, the subject matter of the present disclosure may be embodied in a method of sorting particles in a fluid sample, in which the method includes flowing a fluid sample containing a group of a first type of particle and a group of a second type of particle into a particle sorting region of a microfluidic device, in which the particle sorting region includes a first microfluidic channel, a second microfluidic channel extending along the first microfluidic channel, and a first array of islands separating the first microfluidic channel from the second microfluidic channel, in which a fluidic resistance of the first microfluidic channel relative to the fluidic resistance of the second microfluidic channel changes along a section of the particle sorting region such that a first portion of the fluid sample is siphoned from the first microfluidic channel into the second microfluidic channel through openings between islands in the first array, and in which the first microfluidic channel, the second microfluidic channel and the first array of islands are further arranged to generate inertial lift forces that substantially prevent the group of the first type of particle from propagating with the siphoned fluid portion through the openings of the first array while allowing the group of the second type of particle to propagate with the siphoned fluid portion into the second microfluidic channel.

Implementations of the method may have one or more of the following features. For example, in some implementations, the inertial lift forces shift the group of the first type of particles across fluid streamlines so that the group of the first type of particles continue to propagate with a second portion of the fluid sample remaining in the first microfluidic channel. In some implementations, the first type of particle is larger than the second type of particle. In some implementations, the first portion of the fluid sample passes through the openings in the first array of islands in response to a change in the fluidic resistance between the first microfluidic channel and the second microfluidic channel. The change in the fluidic resistance may include a change in a cross-sectional area of one of the first microfluidic channel or the second microfluidic channel along a direction of fluid flow. The change in the fluidic resistance may include a change in a size of the openings between the islands in the array.

Implementations of the subject matter described herein provide several advantages. For example, in some implementations, the subject matter described herein can be used to isolate particles within a fluid and/or focus particles within a fluid. In some implementations, the subject matter described herein can be used to filter particles from a fluid or shift particles from one fluid to another fluid. High volumetric capacity and throughput, substantial and tunable fluid volume reduction, and high particle yields with inexpensive and simple instruments can be achieved using the techniques described herein. In some implementations, the presently described techniques also may provide streamlined processing and simple integration with other microfluidic modules. For clinical applications, the systems described herein may be configured as both self-contained and disposable. In contrast, for bioprocessing/industrial applications, the devices may be configured for continuous flow/processing.

For the purposes of this disclosure, channel refers to a structure in which a fluid may flow.

For the purposes of this disclosure, microfluidic refers to a fluidic system, device, channel, or chamber that generally have at least one cross-sectional dimension in the range of about 10 nm to about 10 mm.

For the purposes of this disclosure, gap refers to an area in which fluids or particles may flow. For example, a gap may be a space between two obstacles in which fluids flow.

For the purposes of this disclosure, rigid island structure refers to a physical structure through which a particle generally cannot penetrate.

For the purposes of this disclosure, fluidic resistance refers to the ratio of pressure drop across a channel (e.g., a microfluidic channel) to the flow rate of fluid through the channel.

Particles within a sample can have any size which allows them to transported within the microfluidic channel. For example, particles can have an average hydrodynamic size that is between 1 µm and 100 µm. The particle size is limited only by channel geometry; accordingly, particles that are larger and smaller than the above-described particles can be used. The size of particles (e.g., cells, eggs, bacteria, fungi, virus, algae, any prokaryotic or eukaryotic cells, organelles, exosomes, droplets, bubbles, pollutants, precipitates, organic and inorganic particles, magnetic beads, and/or magnetically labeled analytes), such as the average hydrodynamic particle size or average diameter, can be determined using standard techniques well known in the field.

Unless otherwise defined, all technical and scientific terms used herein have the same meaning as commonly understood by one of ordinary skill in the art to which this invention belongs. Although methods, materials, and devices similar or equivalent to those described herein can be used in the practice or testing of the present invention, suitable methods, materials and devices are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments are set forth in the accompanying drawings and the description below. Other features, objects, and will be apparent from the description, drawings, and claims.

DETAILED DESCRIPTION

Figure 1:
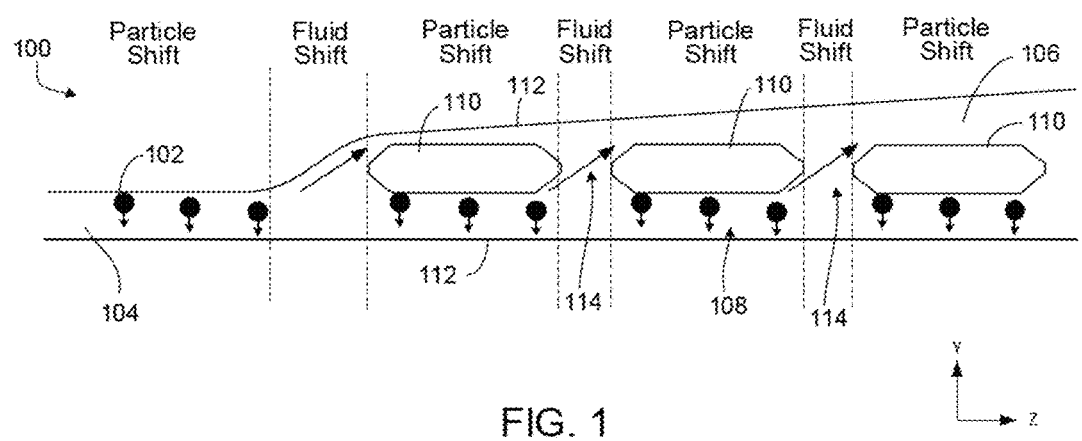
FIG. 1 is a schematic that illustrates a top view of an example of a microfluidic device capable of shifting the position of particles within and across fluid streamlines.

Interactions between particles (e.g., cells, e.g., blood cells in general as well as fetal blood cells in maternal blood, bone marrow cells, and circulating tumor cells (CTCs), sperm, eggs, bacteria, fungi, virus, algae, any prokaryotic or eukaryotic cells, cell clusters, organelles, exosomes, droplets, bubbles, pollutants, precipitates, organic and inorganic particles, beads, bead labeled analytes, magnetic beads, and/or magnetically labeled analytes), the fluids in which they travel (e.g., blood, aqueous solutions, oils, or gases), and rigid structures can be used to shift particles across fluid streamlines in microfluidic devices in a controlled fashion. In particular, forces experienced by particles traveling in a microfluidic device can be used to precisely position the particles, such that a variety of useful microfluidic operations can be performed. Examples of microfluidic operations that can be performed using such forces include, but are not limited to, concentrating particles in a carrier fluid, shifting particles from one carrier fluid to another fluid, separating particles within a fluid based on particle size (e.g., average diameter), focusing particles within a carrier fluid to a single-streamline (or to multiple different streamlines), precise positioning of particles at any position within a microchannel, and mixing (defocusing) particles. Moreover, any of the above operations can be executed simultaneously with other techniques (e.g., magnetic sorting) to enhance the operation's effectiveness.

Several different mechanisms can be employed to create the forces capable of shifting particles across fluid streamlines. A first type of force is referred to as "bumping" (also called deterministic lateral displacement (DLD)). Bumping is direct interaction between a rigid wall of a structure and a particle that arises due to the size of the particle relative to the wall. Since the center of a particle having radius $r_p$ cannot pass closer to an adjacent structure than $r_p$, if the particle center lies on a streamline that is less than $r_p$ from the structure, the particle will be bumped out by the structure to a distance that is at least $r_p$ away. This bumping may move the particle across fluid streamlines.

Another type of force is called inertial lift force (also known as wall force or wall induced inertia). In contrast to bumping, the inertial lift force is a fluidic force on a particle, not a force due to contact with a rigid structure. Though not well understood, the inertial lift force is a repulsive force arising due to a flow disturbance generated by the particle when the particle nears the wall. A particle flowing near a micro-channel wall experiences an inertial lift force normal to the wall. At high flow rates, the inertial lift force is very strong and can shift the particle across streamlines. Furthermore, because the force is highly size-dependent (larger particles experience a much larger force), it can be employed to fractionate particles based on size. Further details on inertial flow can be found in D. Di Carlo, D. Irimia, R. G. Tompkins, and M. Toner, "Continuous inertial focusing, ordering, and separation of particles in microchannels.," Proc. Natl. Acad. Sci. U.S.A., vol. 104, no. 48, pp. 18892-18897, November 2007; D. Di Carlo, J. F. Edd, K. J. Humphry, H. A. Stone, and M. Toner, "Particle segregation and dynamics in confined flows.," Phys. Rev. Lett., vol. 102, no. 9, p. 094503, March 2009; and D. Di Carlo, "Inertial microfluidics," Lab Chip, vol. 9, no. 21, p. 3038, 2009, each of which is incorporated herein in its entirety.

Another type of force is a result of pressure drag from Dean flow. Microfluidic channels having curvature can create additional drag forces on particles. When introducing the curvature into rectangular channels, secondary flows (i.e., Dean flow) may develop perpendicular to the direction of a flowing stream due to the non-uniform inertia of the fluid. As a result, faster moving fluid elements within the center of a curving channel can develop a larger inertia than elements near the channel edges. With high Dean flow, drag on suspended particles within the fluid can become significant.

Another type of force occurs with High Stokes number flow. The Stokes number (Stk) describes how quickly a particle trajectory changes in response to a change in fluid trajectory. For Stk greater than 1, a lag exists between the change in fluid trajectory and the change in particle trajectory. Under high Stokes flow conditions (e.g., a Stokes number greater than about 0.01), changing the fluid flow direction can be used to force particles across streamlines. Further details on Dean flow and high Stokes number can be found, for example, in U.S. Pat. No. 8,186,913, which is incorporated herein by reference in its entirety. In both high Stokes flow applications and Dean flow applications, the fluid displacement causes the particles to cross fluid streamlines.

Other techniques for shifting particles include viscoelastic and inertio-elastic focusing. Details on those methods can be found in "Sheathless elasto-inertial particle focusing and continuous separation in a straight rectangular microchannel," Yang et al., Lab Chip (11), 266-273, 2011, "Single line particle focusing induced by viscoelasticity of the suspending liquid: theory, experiments and simulations to design a micropipe flow-focuser," D'Avino et al., Lab Chip (12), 1638-1645, 2012, and "Inertio-elastic focusing of bioparticles in microchannels at high throughput," Lim et al., Nature Communications, 5 (5120), 1-9, 2014, each of which is incorporated herein by reference in its entirety.

The foregoing techniques are "internal," in that they use fluid flow and/or structures of the microfluidic channel itself to generate the forces necessary to shift particles across streamlines. In some cases, other external mechanisms can also be used in conjunction with one or more of the internal forces to alter the course of particles traveling within a fluid. For example, in some cases, externally applied magnetic forces, gravitational/centrifugal forces, electric forces, or acoustic forces may be used to cause a shift in particle position across fluid streamlines. Further information on how to apply such forces can be found, e.g., in WO 2014/004577 titled "Sorting particles using high gradient magnetic fields," U.S. Pat. No. 7,837,040 titled "Acoustic focusing," WO 2004/074814 titled "Dielectrophoretic focusing," and "Microfluidic, Label-Free Enrichment of Prostate Cancer Cells in Blood Based on Acoustophoresis," Augustsson et al., Anal. Chem. 84(18), Sep. 18, 2012.

The present disclosure focuses primarily on combining inertial lift forces with periodic fluid extraction to shift particles across fluid streamlines for sorting particles between fluids and/or separating particles from fluids. In particular, a particle containing first fluid is introduced into a first microfluidic channel having arrays of rigid island structures separating the first channel from adjacent microfluidic channels. As the first fluid is extracted from the first microfluidic channel into the second microfluidic channel through gaps between the island structures, the particles are drawn nearer to the island structures. As the particles reach nearer to the island structures, the particles experience an inertial lift force away from the direction of fluid extraction such that the particles cross fluid streamlines and remain within the first channel. At the same time, a second fluid passes from a third microfluidic channel through a second array of island structures into the first microfluidic channel, such that the particles in the first channel are transferred to the second fluid within the first channel. In some implementations, the amount of the first fluid entering the second channel from the first channel is the same as the amount of the second fluid entering the first channel from the third channel. As a result, a particle may be shifted from one fluid to another fluid while maintaining the same particle concentration. The combination of fluid extraction and inertial lift forces may be used to perform positioning of particles, particle filtering, particle mixing, fluid mixing, and/or shifting of fluids across particle streams, among other operations.

It should be noted, however, that the techniques described herein for particle and/or fluid sorting are not limited to using inertial lift forces. Instead, periodic fluid extraction also may be combined with one or more of the above-described forces (both internal and external) to control the position of particles within fluids propagating in a microfluidic device.

The mechanisms for shifting particles disclosed herein may also be size-based and therefore can be used to perform size-based manipulation of particles (e.g., based on the average diameter of the particles). Through repeated shifting of particles across streamlines, both fluid and particles in microfluidic devices can be manipulated to perform operations such as focusing particles to one or more fluid streamlines, filtering particles from a fluid, mixing different particles from different fluid streams, and/or sorting particles based on size. In general, "focusing" particles refers to re-positioning the particles across a lateral extent of the channel and within a width that is less than the channel width. For example, the techniques disclosed herein can localize particles suspended in a fluid to a fluid stream, in which the ratio of the channel width to the width of the fluid stream is about 1.05, 2, 4, 6, 8, 10, 20, 30, 40, 50, 60, 70, 80, 90, or 100. Particles may have various sizes including, but not limited to, between about 1 µm and about 100 µm in average diameter.

The mechanisms for shifting particles disclosed herein may also depend on particle shape (e.g., spherical vs. cylindrical) and deformability (e.g., rigid vs. compliant), thereby enabling differential manipulation and sorting of particles based on shape and deformability.

Particle Shifting/Sorting Using Inertial Lift Forces

Prior to discussing how particles may be shifted from one fluid to another using one or more of the devices disclosed herein, it is helpful to first review fluid extraction and inertial forces within the context of a more basic device structure, such as the device shown in FIG. 1. FIG. 1 is a schematic that illustrates a top view of an example of a microfluidic device 100 capable of shifting/sorting the position of particles 102 across fluid streamlines while the fluid propagates through the microfluidic device 100. As will be explained, the particle shifting across fluid streamlines relies on the inertial lift forces experienced by particles as fluid is periodically extracted from a microfluidic channel. For reference, a Cartesian coordinate system is shown, in which the x-direction extends into and out of the page.

During operation of the device 100, a fluid carrying the particles 102 is introduced through an inlet microfluidic channel 104. In this and other implementations of the particle shifting devices, the fluid can be introduced through the use of a pump or other fluid actuation mechanism. The inlet channel 104 splits into a particle sorting region having two different fluid flow channels (second microfluidic channel 106 and first microfluidic channel 108 substantially parallel to the second microfluidic channel 106) that are separated by a 1-dimensional array of rigid island structures 110. The 1-dimensional array of island structures 110 extends substantially in the same direction as the flow of the fluid through the second and first microfluidic channels. Each island structure 110 in the array is separated from an adjacent island 110 by an opening or gap 114 through which fluid can flow. Each gap 114 in the example of FIG. 1 has the same distance between adjacent islands 110. In other implementations, different gaps can have different distances between adjacent islands 110. For example, in some implementations, a length of each subsequent opening (e.g., as measured along the fluid propagation direction—the z-direction in FIG. 1) in the first array is greater than a size of a previous opening in the array. Alternatively, in some implementations, the distance can alternate between larger and smaller for subsequent openings. Furthermore, although a 1-dimensional array is shown in FIG. 1, the islands 110 may be arranged in different configurations including, for example, a two-dimensional array of islands. The boundaries of the fluid flow regions within the microfluidic channels are defined by the device walls 112 and the walls of the islands 110.

As the fluid propagates substantially along the z-direction from the inlet channel 104 to the channels (106, 108), particles 102 experience a force (in this example, an inertial lift force) that causes the particles 102 to shift across fluid streamlines and travel along the first microfluidic channel 108. These inertial lift forces are in the negative y-direction (see short arrows adjacent to each particle 102 in FIG. 1).

For instance, when a particle 102 is located in the inlet channel 104 and approaches the top wall 112, the particle experiences an inertial lift force that pushes the particle down toward the first microfluidic channel 108. Once in the first microfluidic channel 108, the particle 102 may approach a wall of the first island 110, such that it again experiences an inertial lift force pushing the particle 102 down, maintaining the particle within the first microfluidic channel 108. The repeated application of the inertial lift force to the particle 102 in each of the "particle shift" regions shown in FIG. 1 thus serves to separate/filter the particle from the fluid propagating through the second microfluidic channel 106.

At the same time, portions of the fluid traveling in the first microfluidic channel 108 are extracted or flow into the second microfluidic channel at one or more "fluid shift" or "fluid extraction" regions (see FIG. 1) in the device 100. In the example of FIG. 1, each fluid shift region corresponds to an opening or gap that extends between the first microfluidic channel 108 and the second microfluidic channel 106. Each "fluid shift" region primarily allows fluid to be extracted from the first microfluidic channel 108 into the second microfluidic channel 106. The movement of fluid into the gaps tends to pull the particles 102 toward the gaps as well, since the particles follow the fluid streamlines. However, as the particles move closer to the gaps 114, they approach the island structures 112, which impart an inertial lift force causing the incident particles to cross fluid streamlines in a direction away from the gaps 114. That is, the particles 102 shift from a fluid streamline passing into the second microfluidic channel 106 to a fluid streamline that continues to flow in the first microfluidic channel 108. As a result, the particles 102 continue to propagate in the first microfluidic channel 108 and are not shifted into the second microfluidic channel 106 with the fluid. If there were no fluid shifting from the first microfluidic channel 108 to the second microfluidic channel 106, the particles would migrate as a result of inertial focusing. However, by shifting the fluid across the channels, the particles 102 tend to follow the fluid toward areas where the inertial lift force is much stronger than the shear gradient force, thus causing the particles to shift across streamlines in a very efficient and controlled manner.

In the present example, the fluid is extracted through the fluid shift regions as a result of decrease in fluidic resistance. That is, for a fluid of constant viscosity, the gaps 114 between adjacent islands 110 increase the channel area through which the fluid can flow, resulting in a reduced fluidic resistance. As fluid propagates through channel 108 of device 100 and arrives at a gap 114, a portion of the fluid will flow into the gap 114 and subsequently into the second microfluidic channel 106 (i.e., the fluid portion is extracted into channel 106). The decrease in fluidic resistance also can occur as a result of the increasing channel width in the second microfluidic channel 106. In some implementations, the width of channel 106 may be understood as the distance between a position on the second channel wall 112 and a position on a surface of an island 110 directly across from and facing the position on the second channel wall 112. For the gap regions between islands 110, the width of the channel 106 may be understood, in some implementations, as the distance between a position on the second channel wall 112 and a position on an imaginary surface extending through the gap between adjacent islands 110 that is directly across from and facing the position on the channel wall 112, in which the imaginary surface is co-linear with the sides of the adjacent islands closest to and facing the wall 112.

In a particular example, such as shown in FIG. 1, the second microfluidic channel wall 112 is slanted at an angle away from (oriented obliquely with respect to) the islands so that the width of the second microfluidic channel 106 increases along the channel's longitudinal direction (e.g., in the direction of fluid propagation or the positive z-direction for the example shown in FIG. 1), thus causing a decrease in fluidic resistance. Any increase in the cross-sectional area of the channel 106 along the longitudinal direction of the first microfluidic channel, not just an increase in width, also can be employed to reduce the fluidic resistance. Alternatively, or in addition, the fluid may experience an increase in fluidic resistance in channel 108 relative to the fluidic resistance of channel 106 (e.g., through a decrease in the cross-sectional area of the channel 108 along the longitudinal direction).Thus, it may be said that the fluid is extracted in response to a change in the relative fluidic resistance between the second and first microfluidic channels that leads to fluid being extracted from the first channel 108 into the second channel 106. The change in the relative fluidic resistance may occur over the entire particle sorting region or over a portion of the sorting region that is less than the entire particle sorting region. The change in the relative fluidic resistance may occur along the direction of the fluid flow through the particle sorting region (e.g., along a longitudinal direction of the particle sorting region as shown in FIG. 1).

With progressively lower fluidic resistance at the gaps 114 and/or in channel 106, greater amounts of fluid flow into the second microfluidic channel 106. Furthermore, the repeated shifting of fluid into the second channel 106 reduces the amount of fluid in the first channel 108. For the configuration shown in FIG. 1, the repeated fluid extraction thus increases the particle-to-fluid concentration in the first channel 108, while decreasing the concentration of particles in the second microfluidic channel 106, such that the fluid in the second microfluidic channel 106 is "filtered" or "purified."

The resulting focused particle streamline may be coupled to a separate processing region of the microfluidic device 100 or removed from the device 100 for additional processing and/or analysis. Likewise, the "filtered" fluid in the second channel 106 may be coupled to a separate region of the microfluidic device 100 or removed from the device 100 for additional processing and/or analysis. In some implementations, the particles 102 entering the device 100 are "pre-focused" to a desired fluid streamline position that is aligned with the first microfluidic channel 108. By pre-focusing the particles 102 to a desired position, the probability that particles inadvertently enter into the second microfluidic channel 106 can be reduced.

Another advantage of the particle shifting techniques described herein is that it may be used to focus the particles along one or more streamlines. For instance, as previously explained, portions of fluid may be extracted from an initial microfluidic channel into one or more parallel microfluidic channels. In some instances, the parallel microfluidic channels containing the extracted fluid then may be re-combined with the initial microfluidic channel downstream so that the particles are confined to designated streamlines in a single channel. An advantage of this technique of combining fluid shifting with inertial lift force is that particles may be focused to desired positions within the downstream channel (e.g., near the channel wall, at the middle of the channel, or halfway between the channel wall and the middle of the channel, among other positions) by controlling how much fluid is removed from each side of the initial channel, providing increased flexibility to the design and use of microfluidic devices. In contrast, for microfluidic systems based primarily on inertial focusing, one has limited ability to choose the position of the focused stream within the channel.

Figure 2:
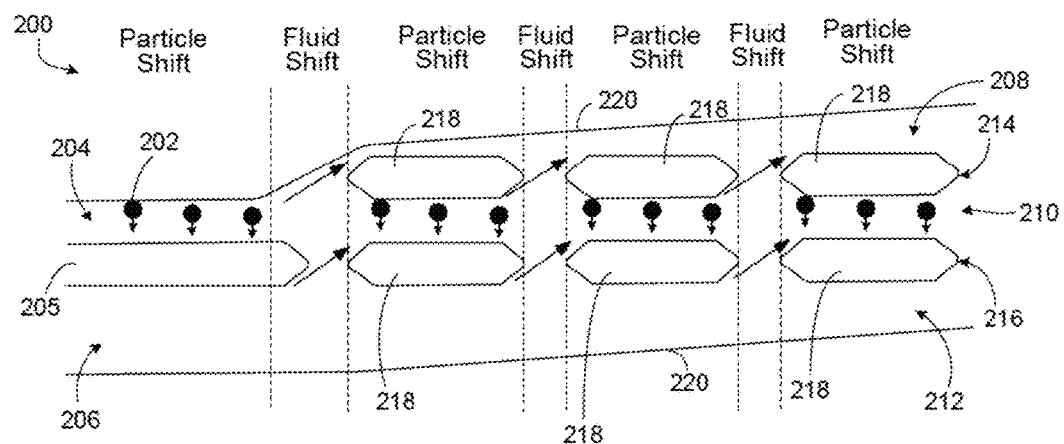
FIG. 2 is a schematic that illustrates a top view of an example of a device for particle and fluid shifting, in which a fluid is allowed to cross over a channel through which particles are propagating.

Having provided a review of fluid extraction and inertial forces, microfluidic devices for shifting/sorting particles between fluids can now be described. In particular, the fluid and particle shifting techniques described herein can be used to shift fluids across channels, without an accompanying shift in particles such that the particles are indirectly transferred to another fluid. FIG. 2 is a schematic that illustrates an example of a device 200 for shifting particles between fluids. The device 200 includes a first inlet microfluidic channel 204 and a second inlet microfluidic channel separated by a dividing structure 205, such as a wall or other object that prevents mixing between the first inlet 204 and the second inlet 206. At the end of the dividing structure 205, the first and second inlet microfluidic channels (204, 206) are fluidly coupled to a particle shifting area that has three different fluid flow regions (a second microfluidic channel 208, a first microfluidic channel 210, and a third microfluidic channel 212).

The second microfluidic channel 208 is separated from the first microfluidic channel 210 by a first array 214 of island structures 218. The third microfluidic channel 212 is separated from the first microfluidic channel 210 by a second array 216 of islands 218. Each adjacent island structure in the first array 214 and each adjacent island structure in the second array 216 is separated by a gap for fluid shifting. The boundaries of the microfluidic channels are defined by the device walls 220 and the walls of the islands. The microfluidic channel wall 220 of the second channel 208 is slanted at an angle away from (oriented obliquely with respect to) the islands 218 so that the width of the second channel increases along the fluid propagation direction, thus causing a decrease in fluidic resistance and leading to extraction of fluid from the first channel 210 into the second channel 208. In contrast, the wall 220 of the third channel 212 is slanted at an angle toward the islands 218 so that the width of the third channel 212 decreases along the fluid propagation direction, thus causing an increase in fluidic resistance, and leading to fluid being extracted from the third channel 212 into the first channel 210.

During operation of the device 200, particles 202 flowing within a first fluid in the first inlet channel 204 interact with the channel walls such that they experience inertial lift forces, which shift or focus the particles 202 toward the center streamlines of the fluid flow. The fluid pathway of the central microfluidic channel 210 is substantially aligned with the fluid pathway of the first inlet channel 204 so the focused particles from channel 204 and a portion of the first fluid flow into the first channel 210. Once the particles 202 enter the first microfluidic channel 210, they experience inertial lift forces from the island structures 218 that continue to focus the particles 202 along one or more central streamlines extending through the channel 210. At the same time, some of the first fluid is extracted into the second microfluidic channel 208 in the "fluid shift" regions due to the reduced fluidic resistance. Because the particles 202 experience inertial lift forces in the first channel 210, the majority of particles 202 remain in the first channel 210 and are not carried with the first fluid into the second channel 208.

A second fluid is provided in the second inlet channel 206. The second fluid may be the same fluid as the carrier fluid used to introduce the particles from inlet channel 204 or a different fluid. The second fluid primarily flows from second inlet 206 into the third microfluidic channel 212. Portions of the second fluid are extracted from inlet 206 and/or third channel 212 into the first microfluidic channel 210 in the "fluid shift" regions. The extraction of the second fluid occurs as a result of the increasing fluidic resistance (e.g., decreasing channel width) the second fluid experiences as the second fluid propagates down channel 212. Accordingly, an increasing amount of the second fluid begins to flow within the first channel 210. In some implementations, e.g., with long enough microfluidic channels, the second fluid may even cross-over from the third microfluidic channel 212 into the first microfluidic channel 210 and finally into the second microfluidic channel 208 to combine with the first fluid. However, because the particles 202 experience the inertial lift forces in the first channel 210, the majority of particles 202 remains in the first channel 210 and are not carried along with the first or the second fluid into the second channel 208. As a result, the combination of the fluid shift regions and the particle shift regions allows isolation of particles 202 from the first fluid. That is, the particles 202 are shifted from the first fluid into the second fluid as the second fluid is introduced into channel 210. Since inertial forces maintain the particles 202 within channel 210, the particles also may be isolated, in certain implementations, from the merged first and second fluids traveling through channel 208.

If the amount of the first fluid extracted from the first channel 210 into the second channel 208 is kept equal to or substantially equal to the amount of the second fluid introduced to the first channel from the third channel over the length of the device, then the amount of fluid propagating through channel 210 may be kept substantially constant. Similarly, since inertial lift forces cause the number of particles propagating through channel 210 to remain substantially constant, the total concentration of particles does not appreciably change even as the fluid changes within channel 210. That is, the concentration of particles 202 within the first fluid at the beginning of the channel 210 is substantially the same as the concentration of particles 202 within the second fluid near the end of the channel 210, after the fluid shift has been completed.

In some implementations, the first fluid is not entirely extracted from channel 210 into channel 208. Rather, the microfluidic device may be configured so that, after operation of the device, there is a combination of both the first fluid and the second fluid within channel 210. In such cases, the first fluid and second fluid may propagate side by side in accordance with laminar flow or may be mixed as a result of, e.g., diffusion. In either instance, if the amount of the first fluid extracted into channel 208 is substantially the same as the amount of second fluid introduced into channel 210 from channel 212 over the length of the device, then the concentration of particles 202 relative to whatever fluids are within channel 210 may be kept substantially constant.

Any of the fluid streams from the second, first, or third channels may be coupled to a separate region of the microfluidic device or removed from the device for additional processing or analysis. In some implementations, the variation in size/fluidic resistance of the second and third channels can be set so as to ensure that equal amounts of fluid flow in from the third channel and out the second channel at each unit.

Figure 3:
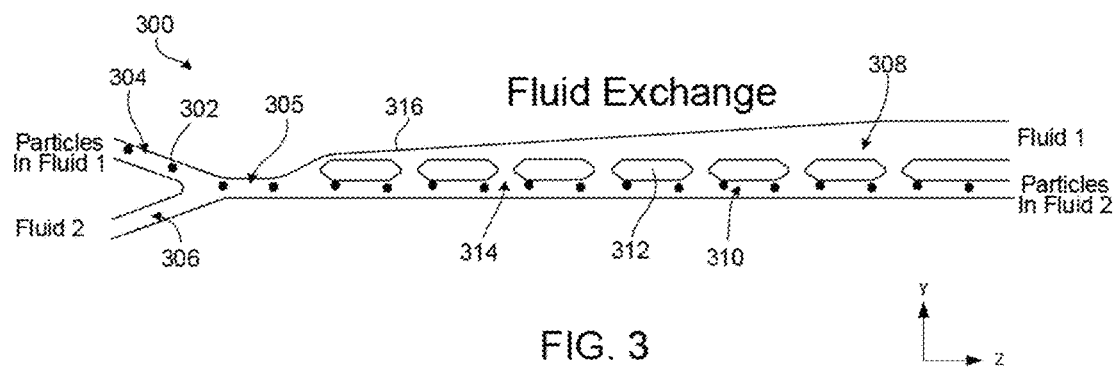
FIG. 3 is a schematic that illustrates a top view of an example of a device having two inlet microfluidic channels coupled to a merging channel, which, in turn, is coupled to a particle shifting area.

Another example of a device capable of causing particles to transition between fluids is shown in FIG. 3, which is a schematic that illustrates an example of a device 300 that includes two inlet microfluidic channels (304, 306) coupled to a single microfluidic channel 305 for merging the fluids. The merging channel 305 is, in turn, coupled to a particle shifting area that includes two different flow regions (second microfluidic channel 308 and first microfluidic channel 310). The second microfluidic channel 308 is separated from the first microfluidic channel 310 by an array of island structures 312, in which each island 312 is separated from an adjacent island 312 by a gap 314 for fluid shifting. In addition, the top wall 316 of the second microfluidic channel 308 is slanted at an angle away from the islands 312 in order to decrease the fluidic resistance along the z-direction.

During operation of the device 300, a first fluid ("Fluid 1") containing particles 302 is introduced in the first inlet channel 304 and a second fluid ("Fluid 2") having no particles is introduced into the second inlet channel 306. Assuming the fluids are introduced at flow rates corresponding to low Reynolds numbers (and thus laminar flow), there is little mixing between the two different fluids in the merge region 305, i.e., the two fluids essentially continue flowing as layers adjacent to one another. The fluid pathway within the merge region 305 is aligned with the fluid pathway of the first microfluidic channel 310 such that the merged fluids primarily flow into the first channel 310. As the two fluids enter the first microfluidic channel 310, the particles 302 within the first fluid experience inertial lift forces from the island structures 312 that are transverse to the direction of flow and that keep the particles 302 within the first microfluidic channel.

At the same time, the increasing width of the second microfluidic channel 308 (due to the slanted channel wall 316) decreases the fluidic resistance, such that portions of the first fluid (which is nearest to the island structures) are extracted into the second channel 308 at each gap between the islands 312. Because the first fluid flows as a layer above the second fluid, little to none of the second fluid is extracted into the second channel 308. After propagating for a sufficient distance past the islands 312, most of the first fluid is extracted into the second channel 308, whereas the particles 302 and most or all of the second fluid remain in the first channel 310. Accordingly, the microfluidic device configuration shown in FIG. 3 is also useful for transferring particles from one fluid to a second different fluid. If the amount of the first fluid flowing through inlet 304 is substantially the same as the amount of the second fluid flowing through inlet 306, then the concentration of particles 302 in the second fluid within channel 310 (and after extraction of the first fluid) can be kept substantially the same as the concentration of particles 302 in the first fluid within the inlet 304. In some implementations, the propagation distance is long enough so that the second fluid also is extracted into the second microfluidic channel 308. In that case, the concentration of the particles 302 in the second fluid within first microfluidic channel 310 can be increased to a level that is higher than the particle concentration within channel 304.

Figure 4:
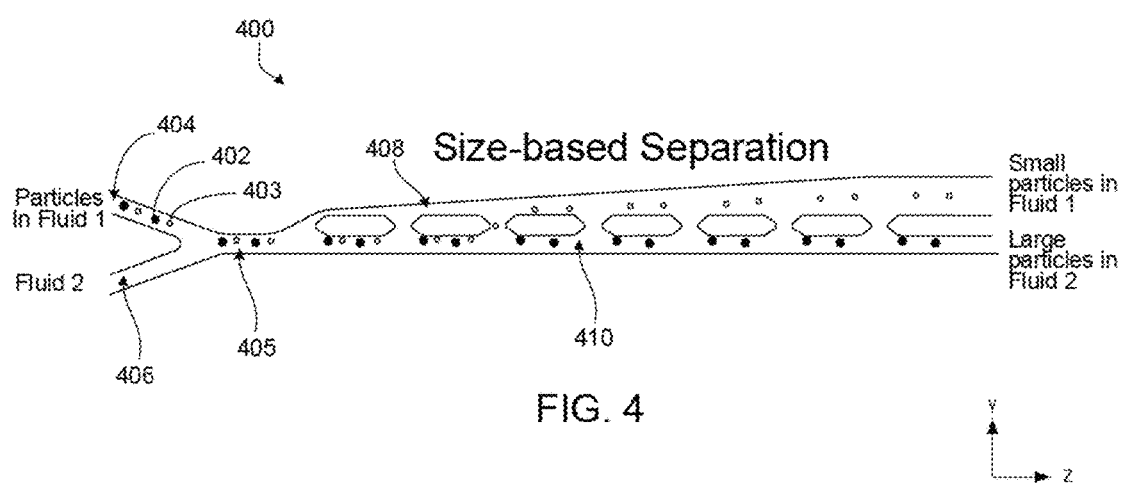
FIG. 4 is a schematic that illustrates a top view of an example of a device having a particle shifting area for size-based sorting of particles.

In some implementations, repeated particle and fluid shifting can be used to perform size-based separation of particles within a fluid. FIG. 4 is a schematic that illustrates an example of a device 400 being used for size-based sorting of particles. The device configuration is identical to the device 300 shown in FIG. 3. During operation of the device 400, a first fluid ("Fluid 1") containing particles of different sizes (large particles 402 and small particles 403) is introduced into in the first inlet channel 404, and a second fluid ("Fluid 2") having no particles is introduced into the second inlet channel 406. The first and second fluids may be the same type or different types of fluids. Again, assuming the fluids are introduced at flow rates corresponding to low Reynolds numbers (and thus laminar flow), there is little mixing between the two different fluids in the merge region 405, i.e., the two fluids essentially continue flowing as layers adjacent to one another. As the two fluids enter the first microfluidic channel 410, the forces on the larger particles 402 are great enough to keep the particles 402 within the first microfluidic channel 410. In contrast, the forces on the smaller particles 403 are not high enough to prevent the small particles 403 from being extracted with the first fluid into the second microfluidic channel 408. After repeated particle shifting and fluid extraction over a sufficient distance, most of the first fluid and the small particles 403 are extracted into the second channel 408, whereas the large particles 402 and most of the second fluid remain in the first channel 410. This process, also called fractionation, is useful for separating particles from a fluid based on size.

There are multiple reasons why large particles 402 are preferentially retained over the smaller particles 403. First, the inertial lift force is highly nonlinear in particle diameter.

For instance, it is believed that near channel walls, the inertial lift force scales in the range of $a^3$ to $a^6$ where a is the particle diameter, such that large particles experience a much larger force than small particles. The larger inertial lift force may be used to move particles out of the fluid streams adjacent to the islands that shift upward from one from one row of the array of island structures to the next. Further information on the relation between particle size and the inertial lift force may be found in Di Carlo et al., "Particle Segregation and Dynamics in Confined Flows", Physical Review Letters, 2009, incorporated herein by reference in its entirety. Second, the equilibrium position of large particles is generally farther from the wall than that of small particles, and therefore is further from the fluid extraction channel and more likely to lie on a streamline that does not shift toward the extraction channel. The large particles therefore may be retained within a given row, whereas smaller particles flowing near the island shift upward from one row of the array to next.

Thus, fractionation is accomplished by repeatedly (1) using the inertial lift force to move large particles away from a channel wall and then (2) shifting the fluid that is free of large particles into an adjacent channel. In some implementations, fractionation can also be used to sort particles from a source fluid (e.g., blood) across fluid streamlines into an adjacent destination fluid (e.g., buffer).

Figure 5:
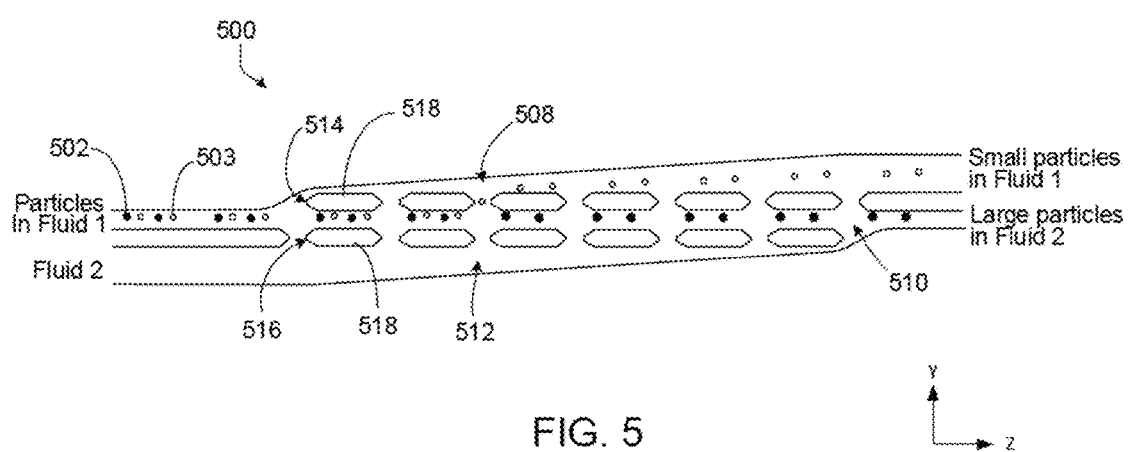
FIG. 5 is a schematic that illustrates a top view of an example of a device having a particle shifting area for size-based sorting of particles.

For instance, FIG. 5 is a schematic illustrating an example of a device 500 that also can be used for separating particles based on size. The configuration of the device 500 is the same as the device 200 shown in FIG. 2. The fluidic resistance in the third microfluidic channel 512 progressively increases due to decreasing channel width, whereas the fluidic resistance of the second microfluidic channel 508 progressively decreases due to increasing channel width. Accordingly, during operation of the device 500, repeated fluid shifting of a first fluid ("Fluid 1") from the first microfluidic channel 510 into the second microfluidic channel 508 occurs at the gaps between islands 518 in the first array 514. Similarly, repeated fluid shifting of a second fluid ("Fluid 2") from the third microfluidic channel 512 into the first microfluidic channel 510 occurs at the gaps between islands 518 in the second array 516. The fluid extraction forces are large enough to pull the small particles 503 along with the first fluid, but not great enough to counter the inertial lift forces experienced by the large particles 502. As a result, the large particles remain flowing along streamlines within the first microfluidic channel 510. After repeated particle and fluid shifting, the large particles 502 begin flowing along streamlines within the second fluid that has been shifted into the first channel 510. If the amount of fluid flowing out of channel 510 into channel 508 is kept substantially equal to the amount of fluid flowing out of channel 512 into channel 510 over the length of the particle sorting/shifting region, then the amount of fluid flowing within channel 510 can be kept substantially constant.

The microfluidic devices shown in FIGS. 1-5 implement particle shifting across fluid streamlines using inertial lift forces from the microfluidic channel walls and from the periodic arrays of island structures. Techniques other than inertial lift force may be used to assist the shift of particles across fluid streamlines. For example, internal forces arising due to high Dean flow and/or high Stokes flow, such as inertial focusing, can be used to shift particles across fluid streamlines and/or to maintain particles within a microfluidic channel. Alternatively, or in addition, external forces such as magnetic forces, acoustic forces, gravitational/centrifugal forces, optical forces, and/or electrical forces may be used to shift particles across fluid streamlines. Additionally, the shape of the rigid island structures that separate different flow regions is not limited to the shapes shown in FIGS. 1-5. For example, the rigid island structures may have shapes similar to posts, cuboids, or other polyhedrons in which the top and bottom faces are, or can be, congruent polygons. In some circumstances, such as at high flow rates, it is advantageous to use islands with streamlined, tapered ends, as this helps minimize the formation of flow recirculations (eddies) that disrupt flow in unpredictable and undesirable ways. Other shapes for the rigid island structures are also possible. The long axis of the rigid island structures may be oriented at an angle with respect to the average flow direction of the fluid, the average flow direction of the particles, or the long axis of the sorting region. The shapes of the channel segments are not limited to the approximately rectangular shapes shown in FIGS. 1-5. The channel segments may include curves or substantial changes in width. In cross-section, the channels described in FIGS. 1-5 may be square, rectangular, trapezoidal, or rounded. Other shapes for the channel cross-sections are also possible. The channel depth may be uniform across the particle sorting region, or the channel depth may vary laterally or longitudinally. Additionally, though FIGS. 1-5 show the microfluidic channels as approximately rectilinear pathways, the channels may be configured in other different arrangements. For example, in some implementations, the microfluidic channels may be formed to have a spiral configuration. For instance, the first microfluidic channel and the second microfluidic channel may be arranged in a spiral configuration, in which the first and second microfluidic channel are still be separated by the array of islands structures, but where the longitudinal direction of fluid flow through the channels would follow a generally spiral pathway. In some implementations, the dimensions or shape of the island structures may vary along the length of the sorting regions (e.g., in the direction of fluid flow) and/or along the width of the sorting regions (e.g., transverse to the direction of fluid flow). In some implementations, the percentage of fluid passing between island structures varies for different locations within the channel. For example, the percentage of fluid may be higher or lower through a first gap between two island structures than the percentage of fluid passing through a next adjacent gap between two island structures.

Although some implementations shown in FIGS. 1-5 include two inlet channels, additional inlet channels may be coupled to the microfluidic channels. In some implementations, three, four or more inlet channels may introduce fluid into the device regions that shift the particles through fluid exchange and inertial lift forces. For example, in some implementations, there may be three inlet channels, one which delivers blood, one which delivers staining reagents, and one which delivers a buffer stream. Using a combination of fluid shifting and inertial lift force techniques disclosed herein, white blood cells from the blood stream could be shifted into the reagent stream and then into a buffer stream.

In some implementations, the devices described herein may be used in conjunction with other microfluidic modules for manipulating fluids and/or particles including, for example, filters for filtering sub-populations of particles of certain sizes. In addition, the devices described herein may be used in series and/or in parallel within a microfluidic system.

Microfluidic Device Design Parameters

Figure 7:
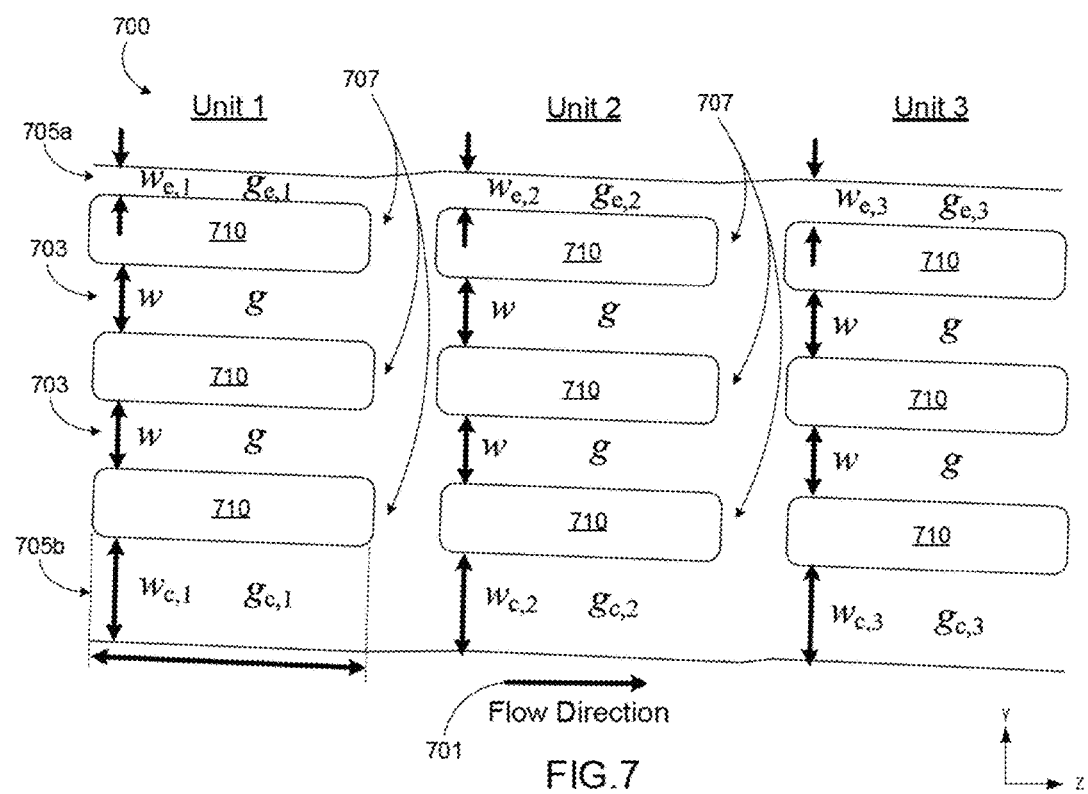
FIGS. 7 and 8 are schematics illustrating top views of example particle sorting regions.

The effect of various design parameters on the operation of the microfluidic device will now be described. For reference, FIG. 7 is a schematic illustrating a top view of an example particle sorting region 700 containing several rows of island structures 710, with each row of islands being separated from an adjacent row of islands by a corresponding interior microfluidic channel 703. Additionally, there is an exterior microfluidic channel 705a extending above the array of islands and an exterior microfluidic channel 705b extending below the array of islands. The primary direction of fluid flow is indicated by the arrow 701. The width of the exterior channel 705a (defined along the y-direction) expands along the length of the channel, whereas the width of the exterior channel 705b (defined along the y-direction) contracts along the length of the channel. For the purposes of the following discussion, the channels and islands may be understood as being arranged into separate "units" (see Unit 1, Unit 2 and Unit 3 in FIG. 7). Specifically, FIG. 7 illustrates three units of an array with two interior channels and two exterior channels.

The relevant design parameters for the particle sorting region 700 are the unit length, width, and fluid shift. Here, the width, w, refers to the dimension of the interior microfluidic channels 703, whereas the length, l, refers to the length of an island structure 710 within a unit. The interior channels thus have fixed width w and fluidic conductance g. The expanding channel has widths $w_{e,i}$ and fluidic conductances $g_{e,i}$, where i refers to the unit number. Similarly, the contracting channel has widths $w_{c,i}$ and fluidic conductances $g_{c,i}$, where i refers to the unit number. The fluid shift, f, is the fraction of the flow, q, in the interior channels that shifts between rows (channels) at each unit. The net flow in the interior channels does not change because at each unit a flow fq (the product of f and q) shifts out of these channels (at the openings 707 between island structures) and a flow fq shifts into these channels (at the openings 707 between island structures). In contrast, the net flow in the exterior channels 705 does change. The net flow in the contracting channel 705b decreases by fq at each unit, and the net flow in the expanding channel 705a increases by fq at each unit. Thus, the widths of the exterior channels of each unit may be set to provide the desired shifting of fluid across the array.

To each successive unit, fg (the product of f and g) is added to the fluidic conductance of the expanding channel and fg is subtracted from the fluidic conductance of the contracting channel. The changing fluidic conductance translates into a proportionate change in volumetric flow rate because the pressure drop per unit, p, is approximately the same across all channels in a unit and flow rate is related to fluidic conductance by the relation q=pg. Therefore, when the conductance of an expanding channel (e.g., channel 705a) increases by fg, the flow rate in the expanding channel increases by fq. Similarly, when the conductance of a contracting channel (e.g., channel 705b) decreases by fg, the flow rate in the contracting channel decreases by fq.

The fluidic conductance of each channel in the array is a function of its dimensions and the fluid viscosity. In the array shown in FIG. 7, each channel is assumed to have a rectangular cross-section and therefore has conductance described by $$g \approx \left(\frac{h^4}{12\eta l\alpha}\right)(1 - 0.63\alpha)$$

Here, $\eta$ is fluid viscosity, l is channel length, w is channel width, h is channel height, and a=h/w. A more accurate infinite series-based formula is also available (Tanyeri et al., "A microfluidic-based hydrodynamic trap: Design and implementation (Supplementary Material)." *Lab on a Chip* (2011).) Computational modeling or empirical methods can be used to determine the conductance of more complex channel geometries. (Note that in this description it is simpler to focus on fluidic conductance, g, rather than fluidic resistance, R. The two quantities are simply related by g=1/R.)

After the fluidic conductance of the interior channel has been determined, the fluidic conductance of the $i^{th}$ unit of expanding channel, $g_{e,i}$, may be expressed as $$g_{e,i} = ifg$$

That is, the fluidic conductance of the first unit is fg, and the fluidic conductance of each successive unit increases by fg. Noting that the flow rate in the $i^{th}$ unit of expanding channel, $q_{e,i}$, is related to the conductance by $q_{e,i} = pg_{e,i}$ and that q=pg, the flow rate in the $i^{th}$ unit of expanding channel may be expressed as $$q_{e,i} = ifq$$

Thus, the flow rate in the first unit is fq, and the flow rate in each successive unit increases by fq.

The fluidic conductance of the $i^{th}$ unit of contracting channel, $g_{c,i}$, may be expressed as $$g_{c,i} = 2g - ifg$$

That is, the fluidic conductance of the first unit is 2g–fg, and the fluidic conductance of each successive unit decreases by fg. Noting that the flow rate of the $i^{th}$ unit of contracting channel, $q_{c,i}$, is related to the conductance by $q_{c,i} = pg_{c,i}$ and that q=pg, the flow rate in the $i^{th}$ unit of expanding channel may be expressed as $$q_{c,i} = 2q - ifq$$

Thus, the flow rate in the first unit is 2q–fq, and the flow rate in each successive unit decreases by fq.

The width of the expanding channel, $w_{e,i}$, is chosen to give the required $g_{e,i}$, and the width of the contracting channel, $w_{c,i}$, is chosen to give the required $g_{c,i}$. In practice, these widths may be determined by evaluating fluidic conductance (using the above formula) across a wide range of channel widths and then interpolating to find the channel width that gives the desired channel conductance.

The number of units needed to increase the flow in the expanding channel to q and decrease the flow in the contracting channel to q is n=1/f. Thus, in the $n^{th}$ unit, the flow rates in all channels are equal: $q_{e,n} = q_{c,n} = q$.

Figure 8:
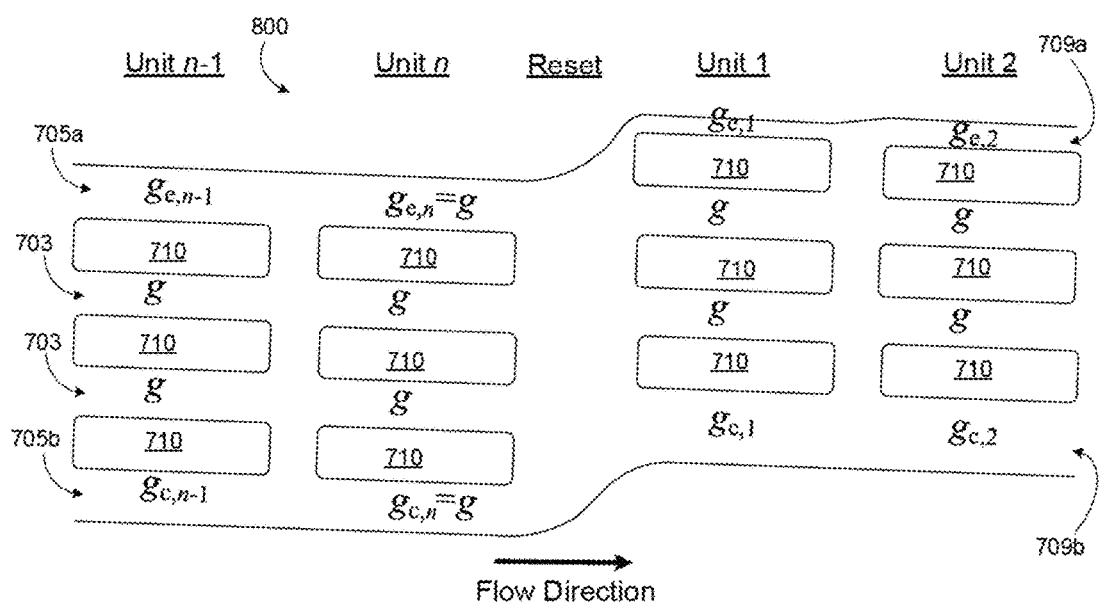
Figures 9A, 9B, 9C, 9D:
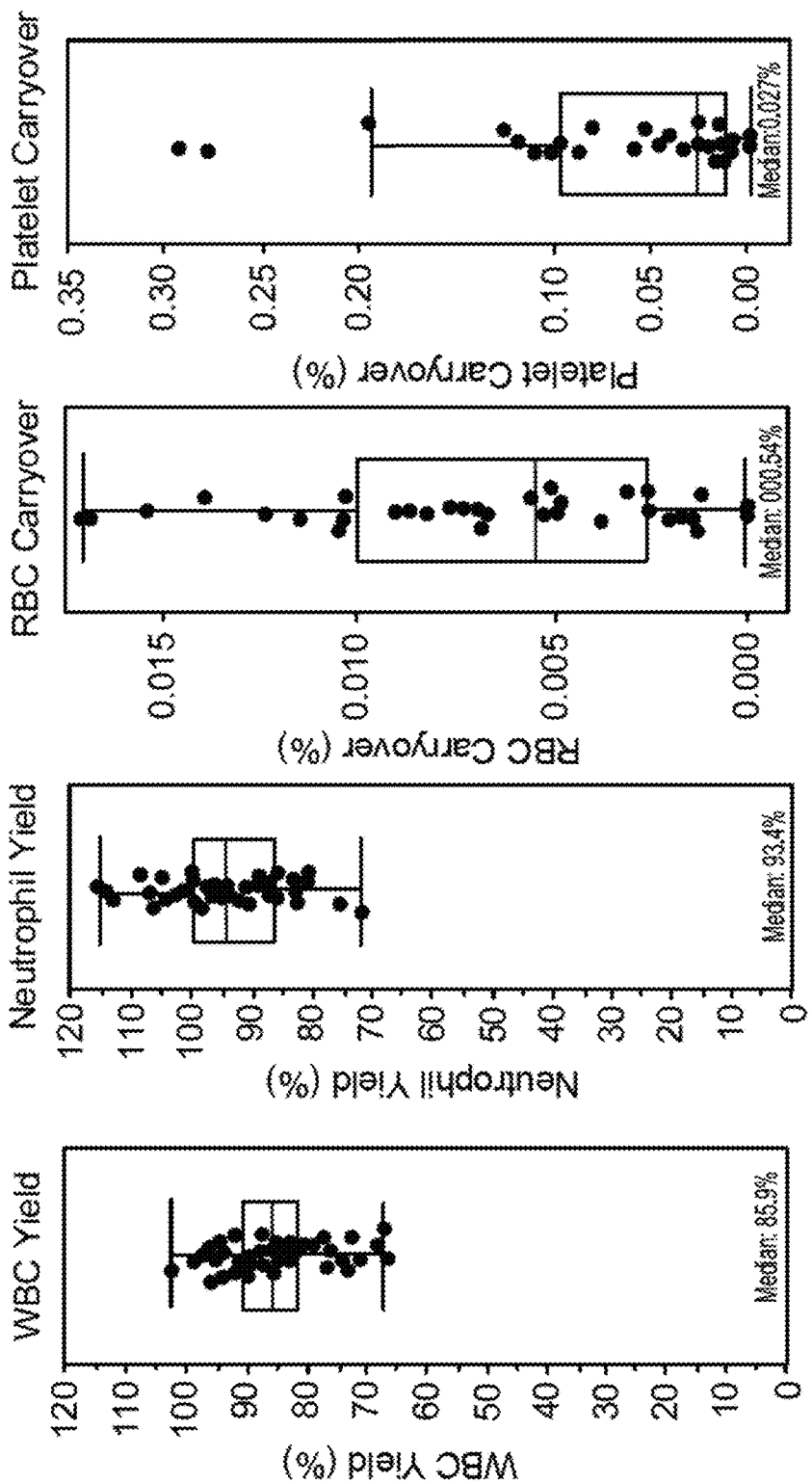
FIG. 9 is a series of plots (FIGS. 9A-9D) illustrating debulking performance for a device that performs fractionation based on inertial lift forces.

After n units, the array may be "reset." For instance, FIG. 8 is a schematic that illustrates a top view of an example particle sorting region 800, similar to the region 700 shown in FIG. 7, in which a "reset" region is introduced after n preceding units of island structures 710. At the reset, the contracting channel 705b and the adjacent interior channel 703 combine to form a new contracting channel 709b, the expanding channel 705a becomes an interior channel, and a new expanding channel 709a is introduced.

The unit length, width, shift, flow speed, and particle size are the factors that most significantly impact performance of the device. Briefly, the impact of each is as follows:

The unit length determines the distance (and time) over which the inertial lift force acts on a particle, and therefore determines the lateral distance that a particle migrates per unit. For a particle to be retained, the unit must be long enough for the particle to escape from the fluid that will be shifted at the next opening between islands.

The flow speed also impacts the magnitude of the inertial lift force and the lateral distance that a particle migrates per unit. The migration (lateral) distance per longitudinal distance is approximately proportional to the flow speed. For a particle to be retained, the flow speed must be fast enough for the particle to escape from the fluid that will be shifted at the next opening between islands.

The shift does not affect particle migration directly, but rather determines how far (i.e., across what fraction of the fluid) a particle must migrate to escape the fluid that will be shifted at the next opening between islands. The larger the shift, the farther a particle must migrate.

The unit width affects performance in two ways. First, the width (and height) of the unit affect the magnitude of the inertial lift force acting on a particle, with the force decreasing as unit width increases. Second, the width relates the shift to the distance a particle must migrate. In other words, for a given shift, the larger the unit width, the farther a particle must migrate to escape the fluid that will be shifted at the next opening between islands.

The magnitude of the inertial lift force is strongly dependent on particle size, with the force increasing dramatically with particle size (D. Di Carlo. "Inertial Microfluidics." Lab on a Chip (2009).). As a result, larger particles laterally migrate farther per unit than smaller particles. It is this difference in migration rates that enables size-based sorting of particles.

For exchanging fluid between channels, the above factors may be chosen to ensure that the particles of interest are retained within the rows of the array. For size-based particle sorting applications, the above factors may be chosen such that a subpopulation of larger particles is retained within the rows while a subpopulation of smaller particles is not.

For instance, the following set of parameters can be used to debulk blood (i.e., separate white blood cells (WBCs) from red blood cells (RBCs) and platelets): unit length of about 200 µm, a unit width of about 50 µm, a unit depth of about 52 µm, about 3.0% shift, and a flow rate of about 80 µL/min per row (0.51 m/s average flow speed). This set of parameters can be highly effective in isolating WBCs with minimal carryover of RBCs and platelets. In this case, white blood cells are spherical and typically >8 µm diameter. Red blood cells are disk shaped with a ~7 µm diameter and ~1.5 µm thickness (and are therefore expected to behave like spheres of intermediate size). Platelets are disk shaped with 3 µm diameter.

The islands have 200 µm length (i.e., same as unit length) and 50 µm width. The purpose of the islands is simply to separate the channels so as to establish the appropriate flow conditions within the device. As such, the width of the islands is not of particular functional importance. The islands could be made somewhat narrower or wider without significantly affecting the performance of the device.

However, the width of the islands does impact ease of manufacturing. Ease of manufacturing is largely determined by the aspect ratio (height divided by width) of structures within a microfluidic device, with smaller aspect ratio devices being easier to manufacture at low cost and with high manufacturing yield. We can define the aspect ratio in two ways. The minimum aspect ratio is the structure height, h, divided by the minimum structure width, $w_{min}$. The overall aspect ratio is the structure height, h, divided by the diameter, D, of a circle with the same area as the structure. Here, D can be expressed as $D=\sqrt{(4A/\pi)}$, where A is the area of the structure.

Because the islands in the example above have 50 µm width and 52 µm height, they have a minimum aspect ratio of 1.04 and an overall aspect ratio of 0.46. This may enable straightforward fabrication of molded PDMS and epoxy devices, as well as injection molded plastic devices. Thus, the device is not only extremely useful from a functional perspective, but it is also fundamentally scalable and economical from a commercial perspective. Furthermore, the set of device parameters listed above can be modified to sort particles of other sizes.

A microfluidic device that is configured to shift particles of a given size can, in some implementations, be scaled to effectively shift particles of a different size. For instance, for a device that employs inertial lift forces to shift particles across fluid streamlines, one can scale the dimensions of the particle shifting area with particle size and alter the flow conditions, so long as the value of the particle Reynolds number, $R_p$, is preserved. The particle Reynolds number can be expressed as:

$$R_p = \frac{U_m a^2}{v D_h}$$

where $U_m$ is the maximum channel velocity, a is the particle diameter, v is the kinematic viscosity of the fluid, and $D_h$ is the hydraulic diameter of the channel. For channels of rectangular cross-section with width w and height h, $D_h$ can be expressed as $(2wh)/(w+h)$, where h is the channel height and w is the channel width. For example, consider a Shifting Area 1 that effectively shifts particles of size a. One method of designing a Shifting Area 2 that effectively shifts particles of size 2a is to scale all dimensions of Shifting Area 1 by a factor of 2 (i.e., double the length, width, and height of all features). To maintain the same $R_p$ in Shifting Area 2, the maximum channel velocity $U_m$ must be decreased by a factor of 2.

Other methods of scaling the dimensions of particle shifting areas and flow conditions with particle size are also possible.

For sorting devices with straight channels that rely on inertial lift forces to shift particles across streamlines, the following provides device design and operation guidelines:

First, as described in "Inertial Microfluidics," Di Carlo, Lab Chip (9), 3038-3046, 2009 (incorporated herein by reference in its entirety), the ratio of the lateral (across channel) particle velocity $U_y$ to the longitudinal (in direction of fluid flow) velocity $U_z$ is proportional to the particle Reynolds number $R_p$ and can be expressed as:

$$\frac{U_y}{U_z} \propto R_p = \frac{U_m a^2}{v D_h}$$

Here $U_m$ is the maximum channel velocity, a is the particle diameter, v is the kinematic viscosity of the fluid, and $D_h$ is the hydraulic diameter of the channel. (For channels of rectangular cross-section with width w and height h, $D_h = (2wh)/(w+h)$.) A goal of the particle sorting device described herein, in some implementations, is to use inertial lift forces to efficiently move particles across streamlines (i.e., maximize $U_y/U_z$). For that purpose, it is recommended that the channel dimensions and flow conditions be selected so as to maximize particle Reynolds number $R_p$ in the particle channel to the extent permitted by other practical constraints, such as operating pressure. Throughout the device, the particle Reynolds number $R_p$ in the particle channel should ideally be greater than about 0.01, though it may be much larger than this, possibly greater than 100. $R_p$ approximately equal to 1 is a good intermediate target.

For a given particle diameter a and kinematic viscosity v, a target particle Reynolds number $R_p$ can be achieved through many different combinations of channel dimensions and channel velocities. One possible strategy for increasing $R_p$ would be to select a very small (relative to a) hydraulic diameter $D_h$. However, channel resistance has a quartic dependence on $D_h$, and choosing an unnecessarily small $D_h$ comes at the cost of highly increased operating pressure. On the contrary, the operating pressure scales linearly with channel velocity $U_m$, so a good alternative strategy is to design a device with a modest hydraulic diameter $D_h$ and then increase channel velocity $U_m$ (and therefore $R_p$) at the time of operation as needed to achieve high yield of particles. For a channel with square cross-section, such that $D_h=w=h$, a value of $D_h$ approximately five times the particle diameter a is a reasonable choice: $D_h=5a$.

Second, the length of the openings (in the longitudinal direction) between islands is preferably, though not necessarily, greater than about a and less than or equal to about w. If the length of the opening is less than a, the opening may clog with particles, thereby disrupting flow through the opening. An opening with length approximately equal to w is unlikely to clog with particles and provides adequate room for fluid to cross between islands to the adjacent channel. An opening with a length greater than w will work but provides no particular benefit and comes at the cost of wasted space.

Third, the length of the islands l is preferably greater than or equal to the length of the openings between islands. Because particles experience inertial lift forces as they travel alongside islands, not at the openings, particles should travel most of their longitudinal distance alongside islands, rather than across openings between islands. Put another way, if the length of islands and the length of the openings between islands are equal, then particles experience inertial lift forces along just 50% of the distance they travel. On the other hand, if the length of the islands is four times the length of the openings, then particles experience inertial lift forces along 80% of the distance they travel.

A loose upper limit on the length of islands l is the length required for particles to migrate to equilibrium focusing positions. Any additional channel length beyond what is required for particles to reach equilibrium does not contribute to shifting particles across streamlines. A formula for the channel length $L_f$ required for particles to reach equilibrium is given in "Inertial Microfluidics," Di Carlo, Lab Chip (9), 3038-3046, 2009 and can be expressed as:

$$L_f = \frac{\pi \mu w^2}{\rho U_m a^2 f_L}$$

Here μ is dynamic viscosity, w is channel width, ρ is fluid density, $U_m$ is the maximum channel velocity, a is the particle diameter, and $f_L$ is a dimensionless constant ranging from about 0.02 to 0.05 for channels with aspect ratios (h/w) ranging from about 2 to 0.5. While $L_f$ provides an upper bound, it is a loose upper bound and exceeds the optimal length of islands l. This is because the lift force on particles is very strong near the channel wall (proportional to $a^6$), but falls off sharply with distance from the wall (proportional to $a^3$ near the center of the channel). Thus, a sorting device will more efficiently shift particles across streamlines if the particles are kept near the channel wall by using an island length l that is significantly less than $L_f$.

Given these considerations, a reasonable intermediate value for the island length is about l=4w. This is an approximate value and necessarily depends on the values selected for other parameters, such as the fluid shift $f_s$.

Fourth, the fluid shift $f_s$ should be greater than 0.2% and ideally greater than 1.0%. If the fluid shift is small, e.g., 0.1%, then the total number of shifts (units) needed to shift particles across the width of the sorting array is very large and the device itself must therefore be very long. Provided the maximum channel velocity $U_m$ is sufficiently high to place the particle Reynolds number $R_p$ in the prescribed range, an extremely small shift, e.g., 0.1%, should not be necessary. Depending on the maximum channel velocity $U_m$, a fluid shift $f_s$ in the range of about 1% to 5% should perform well for a device designed and operated as outlined here.

For any given device design and particle size a, the final parameter choice is the device operating flow rate, which directly determines the maximum channel velocity $U_m$ and the particle Reynolds number $R_p$ in the particle channel. For a device designed as outlined, there will be a lower end flow rate that provides good performance. Below this threshold flow rate, the inertial lift forces will be insufficient to shift particles far enough from the island wall to avoid being shifted with the fluid through the islands, thus resulting in low yield of particles. While the formulas provided here enable one to make rough estimates of the threshold flow rate, the most accurate and relevant method of determining the threshold flow rate is empirically.

If the sorting device is to be used to fractionate particles based on size (i.e., there are two or more populations of particles with different size), then the operating flow rate should be selected such that the inertial lift forces are sufficient to shift the large particles without shifting the small particles.

The design and operating parameter guidelines described here have been found to work well for cell sorting devices. However, other design and optimization strategies may also result in effective, high performance particle sorting devices.

Microfluidic Device Dimensions

For generally spherical particles being transported through a microfluidic device having at least two channels separated by an array of island structures, with gaps between adjacent islands (see, e.g., FIG. 1), the depth (e.g., as measured along the x-direction in FIG. 1) and width (e.g., as measured along the y-direction in FIG. 1) of each microfluidic channel is preferably in the range of about 2 times to about 50 times the diameter of a single particle. With respect to the rigid structures that form the gaps through which fluid is extracted, the width of the structures may be up to about 10 times the width of the a single microfluidic channel, whereas the length of the structures may be between about 0.25 times the channel width up to about 50 times the channel width.

As an example, for a generally spherical particle having a diameter of about 8 microns, a microfluidic device having two microfluidic channels separated by an array of rigid structures similar to the configuration shown in FIG. 1 may have the following parameters: each microfluidic channel and island structure may have a depth of about 50 μm, each microfluidic channel may have a width of about 50 μm, each island structure may have a width of about 50 μm, each island structure may have a length of about 200 μm.

Other examples of dimensions are set forth as follows.

For instance, the distance between the outer walls of the area containing the different fluid flow regions, i.e., as measured transverse to the fluid flow direction, can be configured to be between about 1 µm to about 100 mm (e.g., about 10 µm, about 50 µm, about 100 µm, about 500 µm, about 1 mm, about 50 mm, about 10 mm, or about 50 mm). Other sizes are possible as well. The width of each fluid flow region, measured transverse to the fluid flow direction, can be configured to be between about 1 µm to about 10 mm (e.g., about 50 µm, about 100 µm, about 250 µm, about 500 µm, about 750 µm, about 1 mm, or about 5 mm). Other distances are possible as well.

The length of the gaps/openings between the island structures, as measured along the fluid flow direction (e.g., along the z-direction in FIG. 1), can be configured to be between about 500 nm to about 1000 µm (e.g., about 1 µm, about 2 µm, about 54 µm, about 106 µm, about 50 µm, about 100 µm, about 200 µm, about 500 µm, or about 750 µm). In some implementations, the length of each successive opening is greater than or less than the length of the last opening. For example, in a channel configured to have a decreasing fluidic resistance along the fluid pathway, each successive opening may be larger so that a greater amount of fluid is extracted through the opening. The island structures that separate different fluid flow regions can be configured to have a length between about 10 nm to about 1000 µm, and a width between about 10 nm to about 1000 µm. Other dimensions for the gaps and island structures are possible as well.

The height of the fluid flow regions and the island structures within the particle shifting area (e.g., as measured along the x-direction in FIG. 1) are within the range of approximately 100 nm to approximately 10 mm. For example, the height of the channel can be about 500 nm, about 1 µm, about 5 µm, about 10 µm, about 50 µm, about 100 µm, about 500 µm, about 750 µm, about 1 mm, or about 5 mm. Other heights are possible as well. The microfluidic flow regions can have a cross-sectional area that falls, e.g., within the range of about 1 µm$^2$ to about 100 mm$^2$.

Microfluidic Systems

In some implementations, the particle shifting areas of the microfluidic devices described herein are part of a larger, optional, microfluidic system having a network of microfluidic channels. Such microfluidic systems can be used to facilitate control, manipulation (e.g., sorting, separation, segregation, mixing, focusing, concentration), and isolation of liquids and/or particles from a complex parent specimen. During the isolation process, microfluidic elements provide vital functions, for example, handling of biological fluids or reproducible mixing of particles with samples.

For example, the microfluidic system may include additional areas for sorting particles according to size and/or shape using other techniques different from inertial lift forces. These other techniques can include, for example, deterministic lateral displacement. The additional areas may employ an array of a network of gaps, in which a fluid passing through a gap is divided unequally into subsequent gaps. The array includes a network of gaps arranged such that fluid passing through a gap is divided unequally, even though the gaps may be identical in dimensions. In contrast to the techniques described herein for separating particles based on a combination of inertial lift forces and fluid extraction, deterministic lateral displacement relies on bumping that occurs when the particle comes into direct contact with posts forming the gaps. The flow of the fluid is aligned at a small angle (flow angle) with respect to a line-of-sight of the array. Particles within the fluid having a fluidic size larger than a critical size migrate along the line-of-sight in the array, whereas those having a fluidic size smaller than the critical size follow the flow in a different direction. Flow in the device generally occurs under laminar flow conditions. In the device, particles of different shapes may behave as if they have different sizes. For example, lymphocytes are spheres of ·5 µm diameter, and erythrocytes are biconcave disks of ~7 µm diameter, and ~1.5 µm thick. The long axis of erythrocytes (diameter) is larger than that of the lymphocytes, but the short axis (thickness) is smaller. If erythrocytes align their long axes to a flow when driven through an array of posts by the flow, their fluidic size is effectively their thickness (~1.5 µm), which is smaller than lymphocytes. When an erythrocyte is driven through an array of posts by a fluidic flow, it tends to align its long axis to the flow and behave like a ~1.5 µm-wide particle, which is effectively "smaller" than lymphocytes. The area for deterministic lateral displacement may therefore separate cells according to their shapes, although the volumes of the cells could be the same. In addition, particles having different deformability behave as if they have different sizes. For example, two particles having the undeformed shape may be separated by deterministic lateral displacement, as the particle with the greater deformability may deform when it comes into contact with an obstacle in the array and change shape. Thus, separation in the device may be achieved based on any parameter that affects hydrodynamic size including the physical dimensions, the shape, and the deformability of the particle.

Additional information about microfluidic channel networks and their fabrication can be found, for example, in U.S. Patent App. Publication No. 2011/0091987, U.S. Pat. Nos. 8,021,614, and 8,186,913, each of which is disclosed herein by reference in its entirety.

Figure 6A:
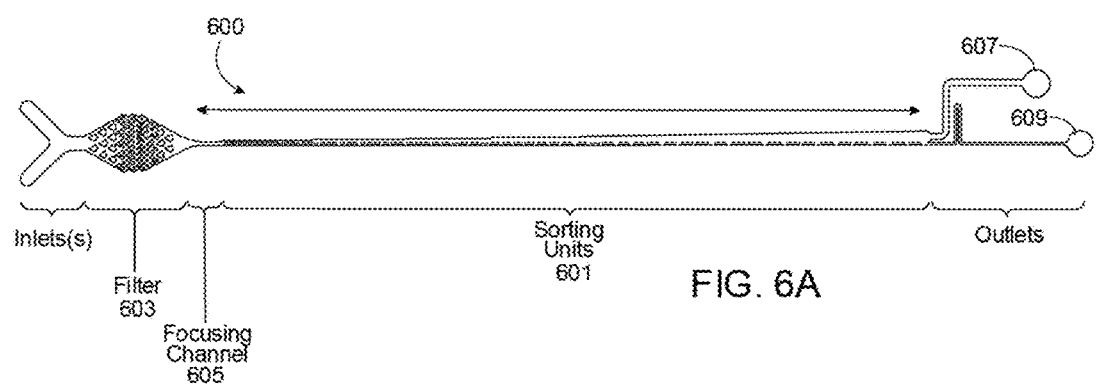
FIG. 6A is a schematic that illustrates a top view of an example of a microfluidic system that includes a particle sorting area.

In some implementations, a microfluidic system includes components for preparing a particle carrying fluid sample prior to introducing the fluid sample into a particle shifting area. For instance, FIG. 6A is a schematic that illustrates a top view of an example of a microfluidic system 600 that includes a particle shifting area 601 (labeled "Sorting Units"), similar to the particle shifting area shown in FIG. 1. Other configurations may be used as the particle shifting area, such as any of the configurations shown in FIGS. 2-5. For configurations that include two or more inlet channels, the system 600 may include an additional fluid source or sources for those inlets.

Figure 6B:
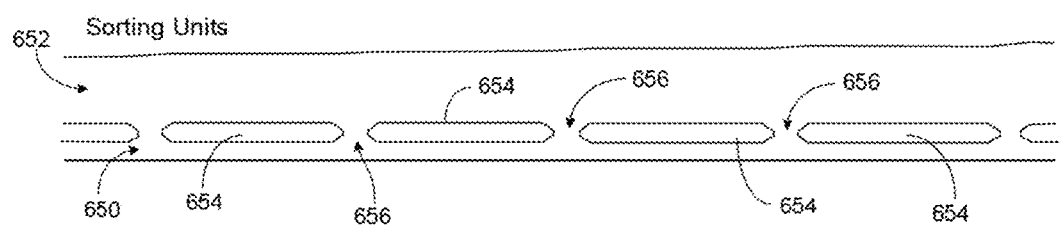
FIG. 6B is an enlarged view of the particle sorting area of FIG. 6A.

FIG. 6B is a schematic that illustrates an enlarged view of the particle sorting region 601. As shown in the enlarged view, the region 601 includes a first microfluidic channel 650 and a second microfluidic channel 652 that extends along the first microfluidic channel 650. The second and first microfluidic channels are separated from one another by an array of island structures 654, in which each island in the array is separated by an adjacent island in the array by a gap or opening 656 that fluidly couples the first microfluidic channel 650 to the second microfluidic channel 652. The fluidic resistance of the area 601 changes along a longitudinal direction of the area 601 (e.g., in the direction of fluid propagation) such that fluid flowing in the first microfluidic channel 650 passes through the openings 656. Inertial lift forces cause particles flowing within the first microfluidic channel 650 near the island structures to cross streamlines so they do not follow the fluid that passes into the second microfluidic channel 652.

The system 600 additionally includes a filter section 603 (labeled "Filter") and a particle focusing section 605 (labeled "Focusing Channel") upstream from the particle shifting area 601. The filter section 603 includes an arrangement of multiple different-sized post structures. Based on the arrangement of the structures, the filter section 603 is configured to filter particles contained in an incoming fluid according to the particle size (e.g., average diameter), such that only particles of a pre-defined size or less are able to pass to the next stage of the system 600. For instance, for complex matrices, such as bone marrow aspirate, the filter section 603 may be configured to remove bone chips and fibrin clots to improve the efficiency of enhancing concentration downstream. In an example arrangement, the filter section 603 may include an array of posts having a pillar size and array offset designed to deflect particles above a certain size, thereby separating them from the main suspension. Typically, the size limit is determined based on the maximum particle size that can pass through later stages of the system 600. For example, the filter 603 may be configured to filter/block passage of particles that have an average diameter greater than 50%, greater than 60%, greater than 70%, greater than 80% or greater than 90% of the minimum width of a channel in the particle shifting area 601.

The filter section 603 is fluidly coupled to the particle focusing section 605. The particle focusing section 605 is configured to pre-focus particles exiting the filter section 603 to a desired fluid streamline position, before the particles are provided to the particle shifting area 601. An advantage of pre-focusing the particles is that it reduces the distribution of particles across the channel width to a narrow lateral extent. The focused line of particles then can be repositioned so that the probability of the particles inadvertently entering the wrong channel within the particle sorting area 601 is reduced (e.g., to avoid the particles entering the second microfluidic channel 652 instead of the first microfluidic channel 650). Pre-focusing can be achieved using inertial focusing techniques. Further details of inertial focusing can be found, for example, in U.S. Pat. No. 8,186,913, which is incorporated herein by reference in its entirety.

Once the particles have been sorted in the particle shifting area 601, the sorted particles may be coupled to separate processing regions of the microfluidic system 600 or removed from the system 600 for additional processing and/or analysis. For example, the second channel of the particle shifting area 601 is coupled to a first outlet 607, whereas the second channel of the particle shifting area 601 is coupled to a second outlet 609.

External Forces

Other functionality may be added to the microfluidic system to enhance the focusing, concentrating, separating, and/or mixing of particles. For instance, in some implementations, additional forces may be introduced which result in target specific modification of particle flow. The additional force may include, for example, magnetic forces, acoustic forces, gravitational/centrifugal forces, electrical forces, and/or inertial forces.

Fabrication of Microfluidic Devices

A process for fabricating a microfluidic device according to the present disclosure is set forth as follows. A substrate layer is first provided. The substrate layer can include, e.g., glass, plastic or silicon wafer. An optional thin film layer (e.g., $SiO_2$) can be formed on a surface of the substrate layer using, for example, thermal or electron beam deposition. The substrate and optional thin film layer provide a base on which microfluidic regions may be formed. The thickness of the substrate can fall within the range of approximately 500 μm to approximately 10 mm. For example, the thickness of the substrate 210 can be 600 μm, 750 μm, 900 μm, 1 mm, 2 mm, 3 mm, 4 mm, 5 mm, 6 mm, 7 mm, 8 mm, or 9 mm. Other thicknesses are possible as well.

After providing the substrate layer, the microfluidic channels formed above the substrate layer. The microfluidic channels include the different fluid flow pathways of the particle shifting area, as well as the other microfluidic components of the system, including any filtering sections, inertial focusing sections, and magnetophoresis sections. Microfluidic channels for other processing and analysis components of a microfluidic device also may be used. The microfluidic channels and cover are formed by depositing a polymer (e.g., polydimethylsiloxane (PDMS), polymethylmethacrylate (PMMA), polycarbonate (PC), or cyclo olefin polymer (COP)) in a mold that defines the fluidic channel regions. The polymer, once cured, then is transferred and bonded to a surface of the substrate layer. For example, PDMS can be first poured into a mold (e.g., an SU-8 mold fabricated with two step photolithography (MicroChem)) that defines the microfluidic network of channels. The PDMS then is cured (e.g., heating at 65° C. for about 3 hours). Prior to transferring the solid PDMS structure to the device, the surface of the substrate layer is treated with $O_2$ plasma to enhance bonding. Alternatively, the microfluidic channels and cover can be fabricated in other materials such as glass or silicon.

Applications

The new microfluidic techniques and devices described herein can be used in various different applications.

Centrifugation Replacement

The particle shifting techniques and devices disclosed herein can be used as replacements for centrifugation. In general, centrifugation is understood to include the concentrating of sub-components within a fluid through the application of centrifugal forces to the fluid. Typically, this process requires devices that have moving parts, which are prone to wear and breakage. Moreover, the moving parts require complex and costly fabrication processes. Another problem with centrifugation is that it is a process typically applied in a closed system, i.e., centrifugation requires manually transferring samples to and from a centrifuge.

In contrast, the presently disclosed techniques are capable of substantially increasing the concentration of fluid components using relatively simple micro-structures without the need for moving parts. The techniques can be implemented as part of a single open microfluidic system, such that fluid samples may be transferred to or from the particle shifting area without manual interference. Additionally, particle shifting can be extended to devices requiring large throughput (i.e., volume rate of fluid that can be processed) without a substantial degradation in particle separation efficiency. For example, the devices disclosed herein may be configured to enable up to 10, 25, 50, 75, 100, 250, 500, 1000, 5000, or 10000 μl/min of fluid flow. Other flow rates are also possible. For instance, using device 100 in FIG. 1 as an example, if the second and first microfluidic channels 106, 108 have depths of approximately 50 μm and widths of approximately 50 μm, the device 100 may be capable of achieving a combined sample flow rate of up to about 5 mL/min. Varying the channel sizes may alter the maximum volumetric flow rate of which the device is capable. Additionally, or as an alternative, the volumetric flow rate may be adjusted by varying the length of the island structures (see section "Microfluidic Device Design Parameters" above). Furthermore, multiplexing multiple channels (e.g., operating multiple particle sorting regions in parallel) may enable even higher rates of flow.

In some implementations, the particle shifting techniques allow separation of particles based on size. For instance, in a fluid sample containing two different sized particles, the particle sorting region described according to the present disclosure may be used to separate the larger particles from the smaller particles (e.g., by siphoning the smaller particles from the fluid sample into an adjacent microfluidic channel while using inertial lift forces to maintain the larger particles in the original microfluidic channel). In another example, a fluid sample may include particles of three or more different sizes, in which the particle sorting region is designed to sort the particles into different regions based on their different sizes.

Thus, in certain implementations, the particle shifting techniques may provide substantial cost and time saving advantages over traditional centrifugation processes. Examples of applications where a microfluidic replacement for a centrifuge device may be useful include bone marrow and urine analysis.

Detecting Infectious Agents

In addition, the particle shifting techniques disclosed herein can be used as part of a research platform to study analytes of interest (e.g., proteins, cells, bacteria, pathogens, and DNA) or as part of a diagnostic assay for diagnosing potential disease states or infectious agents in a patient. By separating and focusing particles within a fluid sample, the microfluidic device described herein may be used to measure many different biological targets, including small molecules, proteins, nucleic acids, pathogens, and cancer cells. Further examples are described below.

Rare Cell Detection

The microfluidic device and methods described herein may be used to detect rare cells, such as circulating tumor cells (CTC) in a blood sample or fetal cells in blood samples of pregnant females. For example, the concentration of primary tumor cells or CTCs can be enhanced in a blood sample for rapid and comprehensive profiling of cancers. By combining the particle deflection techniques described herein with magnetophoresis, different types of cells can be detected (e.g., circulating endothelial cells for heart disease). Thus, the microfluidic device may be used as a powerful diagnostic and prognostic tool. The targeted and detected cells could be cancer cells, stem cells, immune cells, white blood cells or other cells including, for example, circulating endothelial cells (using an antibody to an epithelial cell surface marker, e.g., the Epithelial Cell Adhesion Molecule (EpCAM)), or circulating tumor cells (using an antibody to a cancer cell surface marker, e.g., the Melanoma Cell Adhesion molecule (CD146)). The systems and methods also can be used to detect CTC clusters, small molecules, proteins, nucleic acids, or pathogens.

Fluid Exchange

The microfluidic device and methods described herein may be used to shift cells from one carrier fluid to another carrier fluid. For example, the particle shifting techniques disclosed could be used to shift cells into or out of a fluid stream containing reagents, such as drugs, antibodies, cellular stains, magnetic beads, cryoprotectants, lysing reagents, and/or other analytes.

A single particle shifting region could contain many parallel fluid streams (from many inlets) through which a shifted cell would pass. For example, white blood cells could be shifted from a blood stream into a stream containing staining reagents and then into a buffer stream.

In bioprocessing and related fields, the devices and techniques described may be used to enable sterile, continuous transfer of cells from old media (containing waste products) into fresh growth media. Similarly, extracellular fluids and cellular products (e.g., antibodies, proteins, sugars, lipids, biopharmaceuticals, alcohols, and various chemicals) may be extracted from a bioreactor in a sterile, continuous manner while cells are retained within the bioreactor.

Separating and Analyzing Cells

The microfluidic device and methods described herein may be used to fractionate cells based on biophysical properties, such as size. For example, the device and methods may be used to fractionate blood into separate platelet, red blood cell, and leukocyte streams. In another example, the device and methods may be used to fractionate leukocytes into its separate lymphocyte, monocyte, and granulocyte streams.

The streams of fractionated cells may be isolated by routing them into separate fluid outlets. Alternatively, the streams of cells may be detected and analyzed in real-time (e.g., using optical techniques) to determine the number of cells in each stream or properties, such as size or granularity, of the cells in each stream.

Techniques may be used to alter cells or their carrier fluid before or during sorting to facilitate their fractionation and/or analysis. For example, large beads may be bound to a specific cell type increase the effective size of that cell type. Controlled cell aggregation may also be used to increase the effective size of cells. The temperature, density, viscosity, elasticity, pH, osmotic, and other properties of the fluid may be changed to either directly affect the sorting process (e.g., inertial effects are viscosity dependent) or indirectly affect the sorting process by altering the properties of cells (e.g., osmotic swelling or shrinking).

Fluid Sterilization and Cleansing

The microfluidic device and methods described herein may be used to remove pathogens, pollutants, and other particular contaminants from fluids. By shifting contaminants across fluid streamlines, contaminants may be removed from a fluid sample and collected as a separate waste stream.

Harvesting Algae for Biofuels

Harvesting algae from growth media is a major expense in the production of biofuels because algae grow in very dilute suspensions at near neutral buoyancy, making efficient extraction and concentration of algal biomass difficult. The microfluidic device and methods described herein can provide an efficient means of harvesting algae that does not depend on either density or filtration. The devices and techniques described enable the algae in a growth tank to be extracted from the growth media and concentrated to a high volume density. This could be done either as a single step or as part of a continuous process. Additionally, because the devices described herein can sort cells in a size-dependent manner, they may be designed to sort and concentrate only the larger algae that have reached maturity, returning smaller, immature algae to the tank.

Micro Heat Exchangers

The devices and methods described herein can be used to process not only liquid flows, but also gaseous and multi-phase flows. One example application of interest is in high efficiency heat exchangers for integrated circuits. The high power density in microchips necessitates efficient removal of waste heat. Such cooling becomes increasingly difficult as microchips are stacked, decreasing the overall surface to volume ratio. Liquid cooling, in which heat passes from a heat source into a flowing liquid, is one approach for increasing the cooling rate of microchips. Such cooling can be particularly efficient near the boiling point of the liquid, as considerable energy is absorbed in the liquid to vapor phase change. However, accumulation of vapor (bubbles) at the heat exchange surface dramatically reduces heat flux. The devices and techniques described herein could be used to sweep bubbles away from the heat exchange surface, maximizing heat absorbance by the liquid (via phase change) while minimizing the fraction of the surface in contact with vapor. For this application, one side of the sorting module would contact the microchip heat source. As liquid flowing through module absorbed heat, bubbles would form on the heat exchange surface and then be swept into the flow (by fluid drag) upon reaching a critical size. The sorting array would then direct these bubbles across the sorting module and away from the heat exchange surface, thereby maximizing heat flux from the microchip to the cooling liquid.

EXAMPLES

The invention is further described in the following examples, which do not limit the scope of the invention described in the claims.

Example 1

Debulking

Debulking is the removal of plasma, red blood cells (RBCs), platelets, and other small components (e.g., magnetic beads) from nucleated cells (e.g., white blood cells (WBCs)) in blood and other complex fluids, such as bone marrow aspirate (BMA). This is typically achieved by density centrifugation, which separates blood into layers by density. However, in the following examples, we describe the use of a sorting device that relies on inertial lift forces to debulk blood.

Device Fabrication

For fabricating the microfluidic device, standard SU8 photolithography and soft lithography techniques were used to fabricate the master mold and the PDMS microchannels, respectively. Briefly, negative photoresist SU8-50 (Microchem Corp, Massachusetts) was spun at 2850 RPM to a thickness of approximately 50 μm, exposed to ultraviolet light through a mylar emulsion printed photomask (Fineline Imaging, Colorado) that defines the microfluidic network of channels, and developed in BTS-220 SU8-Developer (J.T. Baker, New Jersey) to form a raised mold. A 10:1 ratio mixture of Sylgard 184 Elastomer base and curing agent (Dow Corning, Michigan) was then poured over the raised mold, allowed to cure in an oven at 65° C. for 8 hours and then removed from the SU8 master mold to form the microfluidic device cover having the patterned channels. Inlet and outlet holes to the channels were punched using custom sharpened needle tips. The devices were then cleaned of particulate using low-residue tape and oxygen plasma bonded to pre-cleaned 1 mm thick glass microscope slides.

The devices had the following parameters: 200 μm unit length, 50 μm unit width, 52 μm unit depth (according to the unit length design discussed above with respect to FIG. 7). The island structures had a length of 200 μm (i.e., same as unit length) and a width of 50 μm.

Sample Preparation

The performance of the debulking device was evaluated across a large number (n=63) independent experiments. In each experiment, ≥2 mL of fresh whole blood with either EDTA or ACD anticoagulant was diluted 1:1 with PBS (1×) with 1% F68 Pluronic.

Experimental Procedure and Results

For each run, the blood sample was driven into the device using a syringe pump operating at 60 μL/min. The buffer coflow (PBS (1×) with 1% F68 Pluronic) was driven into the device using a syringe pump operating at 272 μL/min. The compositions of the input, product, and waste were analyzed using a hematology analyzer (Sysmex KX21N). Manual counting using Neubaur and Nageotte chambers was also performed on the product and waste to ensure accurate data for cell types present in low concentrations (specifically WBCs in the waste and RBCs and platelets in the product).

The data resulting from the experiments is summarized in FIGS. 9A-9D. The median WBC yield is 85.9% and the median neutrophil yield is 93.4%. That the neutrophil yield is somewhat higher than the overall WBC yield is consistent with the fact that neutrophils are the largest WBC subpopulation in physical size. The purity of the product is excellent. The median carryover of RBCs (i.e., percentage of input RBCs that end up in the product) is just 0.0054%, and the median carryover of platelets is just 0.027%, indicating very few RBCs and platelets remain in the same fluid streams as the WBCs and neutrophils. In contrast to some other approaches to microfluidic fraction, the approach presented here is sensitive to the flow rate in the device. This is because the inertial lift force is strongly dependent on flow speed. In the array, the relevant flow rate is the flow rate per row.

Figure 10A:
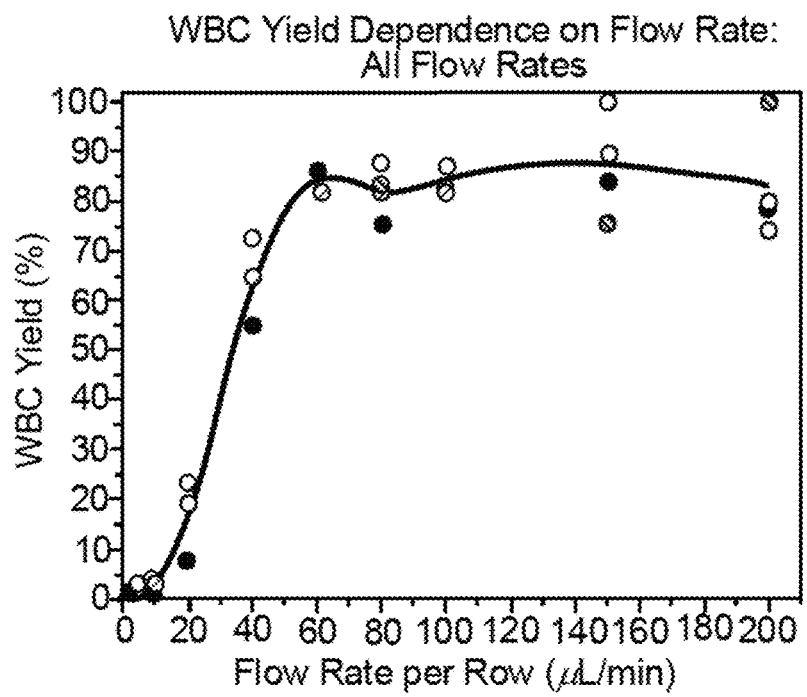
FIG. 10 is a series of plots (FIGS. 10A-10B) of white blood cell (WBC) yield against fluid flow rate.
Figure 10B:
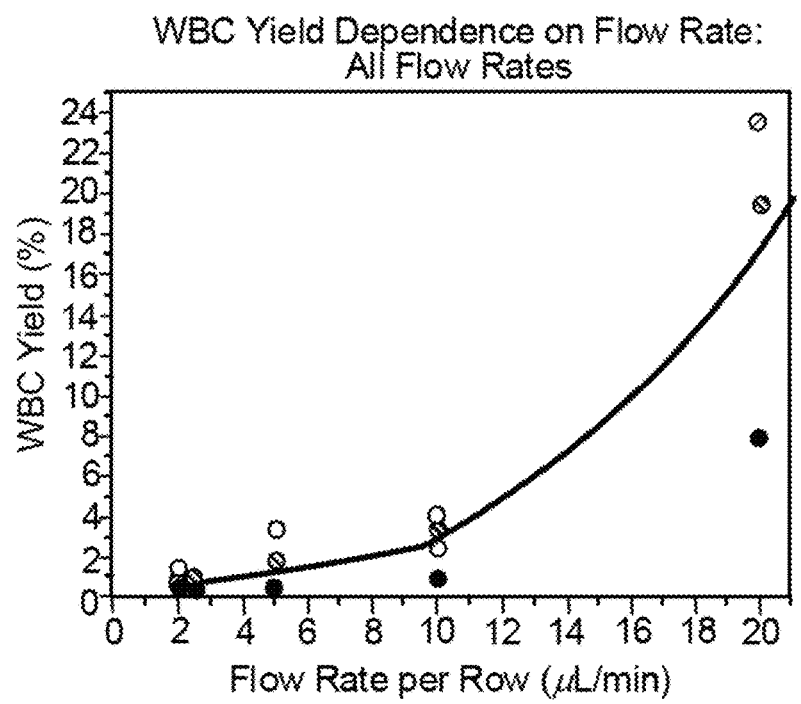

Additional experiments were performed where the flow rate was varied to evaluate the effect on debulking. FIGS. 10A-10B show the WBC yield plotted against the flow rate per row. At low flow rates (<10 μL/min), the inertial lift force is too weak to move WBCs out of the shifted fluid streams, and therefore the yield is ~0%. As the flow rate increases toward 60μL/min, the inertial lift force increases and a larger percentage of WBCs escape the shifted fluid streams and thereby reach the product, increasing the yield. At the highest flow rates (>60μL/min), the inertial lift force is large enough to vector the large majority of WBCs across the array and into the product, with the WBC yield plateauing at ~85%. For reference, the flow rate per row in the debulking experiment of FIG. 9 was 80 μL/min.

The strong dependence of WBC yield on flow rate suggests that it may possible to control the fractionation size threshold by modulating the flow rate per row. For any given flow rate, the inertial lift force on a particle depends on its size. Therefore, we would expect that the curve shown in FIGS. 10A-10B would shift left for larger cells (or subpopulations of larger cells within the WBC population) and that the curve would shift right for smaller cells (or subpopulations of smaller cells within the WBC population). Operating at a flow rate per row large enough to move large cells (e.g., neutrophils) across the array but not large enough to move small cells (e.g., lymphocytes) across the array may be a way of isolating particular subpopulations of cells with high purity.

Example 2

Evaluating Impact of Particle Size, Fluid Flow Rate, and Fluid Shift

The impact of the design and process factors on device performance can be illustrated using two experiments. The first uses fluorescent beads to show the impact of particles size and flow rate per row on yield, and the second uses white blood cells (WBCs) to show the impact of the shift on yield. The device used for the experiments was fabricated according to the same procedure as set forth above in Example 1.

For the first experiment, fluorescent beads of several different sizes were used across a range of flow rates per row. Each bead size was tested independently. In each case, a sample including beads suspended in buffer (PBS (1×) with 1% F68 Pluronic), entered the device alongside a stream of buffer.

Figure 11:
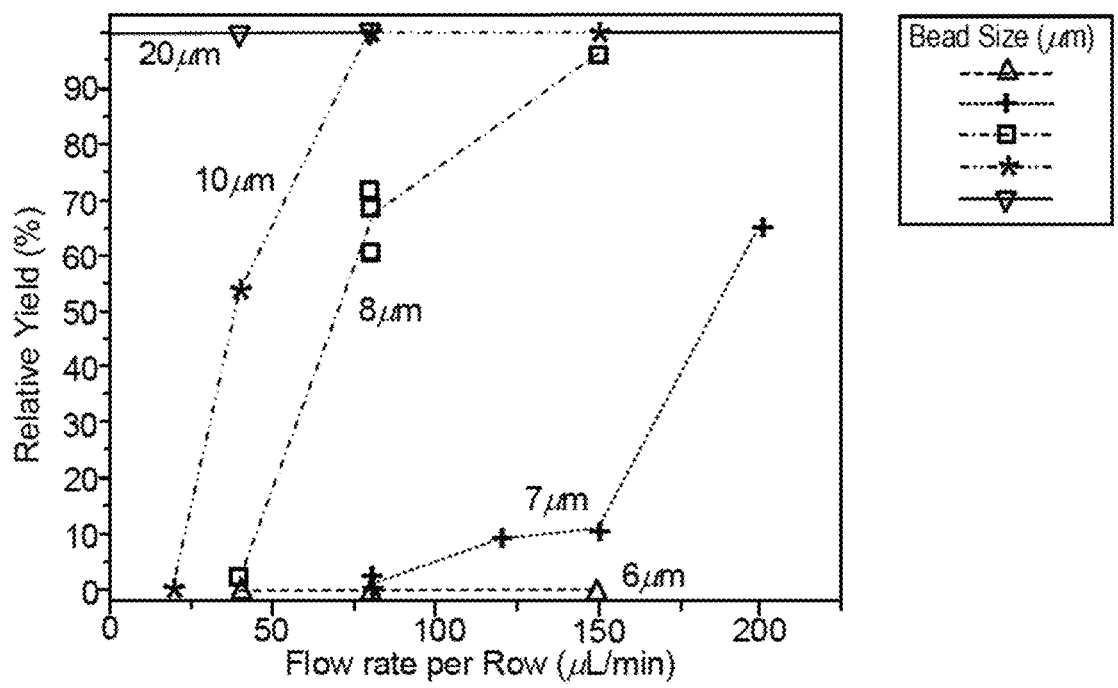
FIG. 11 is a plot of yield of different sized fluorescent beads across different flow rates.

FIG. 11 shows the yield of the different sized fluorescent beads across the different flow rates. The total flow rate (sample+buffer) was chosen to give the indicated flow rate per row, and the relative input flow rates of the sample and buffer were chosen such that 18% of the total input flow was sample. At the end of the device, particles that had migrated downward exited the device through the product channel and were collected in a vial. Particles that remained at the top of the array exited the device through the waste channel and were collected in a separate vial. The volumes of the product and waste vials were measured by mass, and the concentrations of the particles were determined using standard Neubauer and Nageotte counting chambers. The relative yield was calculated as the fraction of output beads in the product.

A few trends stand out in the resulting data. First, for any given bead size, the yield increases with flow rate. This is due to the increase in the inertial lift force with flow speed. Second, for any given flow rate, the yield increases with bead size. This is due to the dramatic increase in inertial lift force with particle size. Taking 80 μL/min per row as an example, the yield is 100% for 20 μm and 10 μm beads. This then drops to 68% for 8 μm beads, 1% for 7 μm beads, and 0% for 6 μm beads. Third, for any given device, the flow rate per row provides a means of fine-tuning the critical particle size. For example, to separate 10 μm particles from ≤7 μm particles, 80 μL/min is the ideal flow rate per row. To separate 8 μm particles from ≤6 μm particles, 150 μL/min is the ideal flow rate per row.

In the second experiment, the impact of fluid shift on the yield of WBCs was evaluated. WBCs were isolated using hetastarch sedimentation. Specifically, 1 mL of 6% hetastarch (Stemcell Technologies HetaSep) was added to 10 mL of fresh whole blood, mixed, and left to sediment for 30 minutes. The top, WBC-enriched (and RBC-depleted) layer was then aspirated with a pipette. This sample was introduced into one of six different devices, each of which had a different shift (2.5%, 3.0%, 3.2%, 3.4%, 3.6%, or 4.0%) and dimensions as described above. In each case, the sample entered the device alongside a stream of buffer. The total flow rate (sample+buffer) was chosen to give 80 μL/min flow rate per row, and the relative input flow rates of the sample and buffer were chosen such that 18% of the total input flow was sample. At the end of the device, WBCs that had migrated downward (across the array) exited the device through the product channel and were collected in a vial. WBCs that remained at the top of the array exited the device through the waste channel and were collected in a separate vial. The volumes of the product and waste vials were measured by mass, and the concentrations of the WBCs were determined using standard Neubauer and Nageotte counting chambers. The relative yield was calculated as the fraction of output WBCs in the product.

Figure 12:
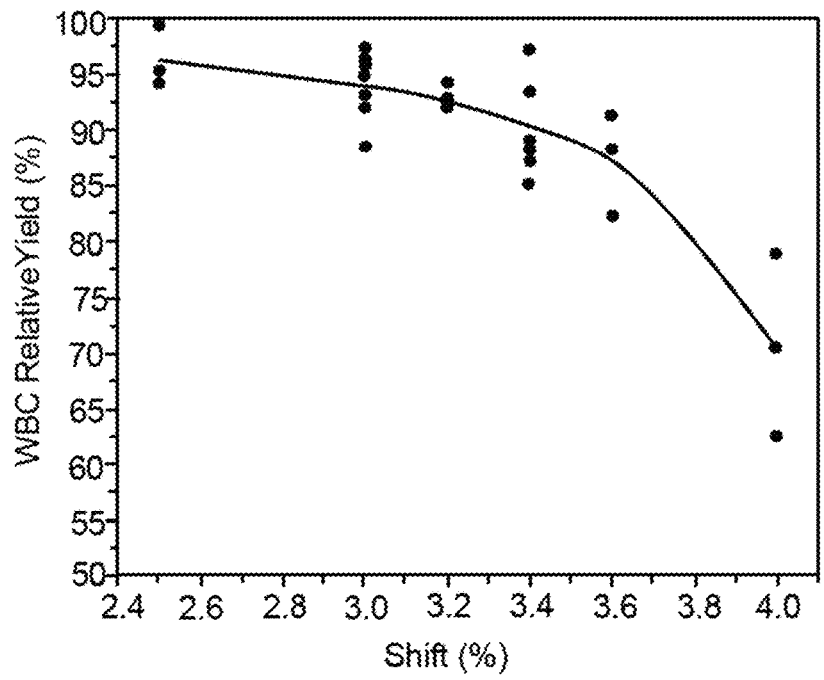
FIG. 12 is a plot of WBC yield versus fluid shift.
Figure 13:
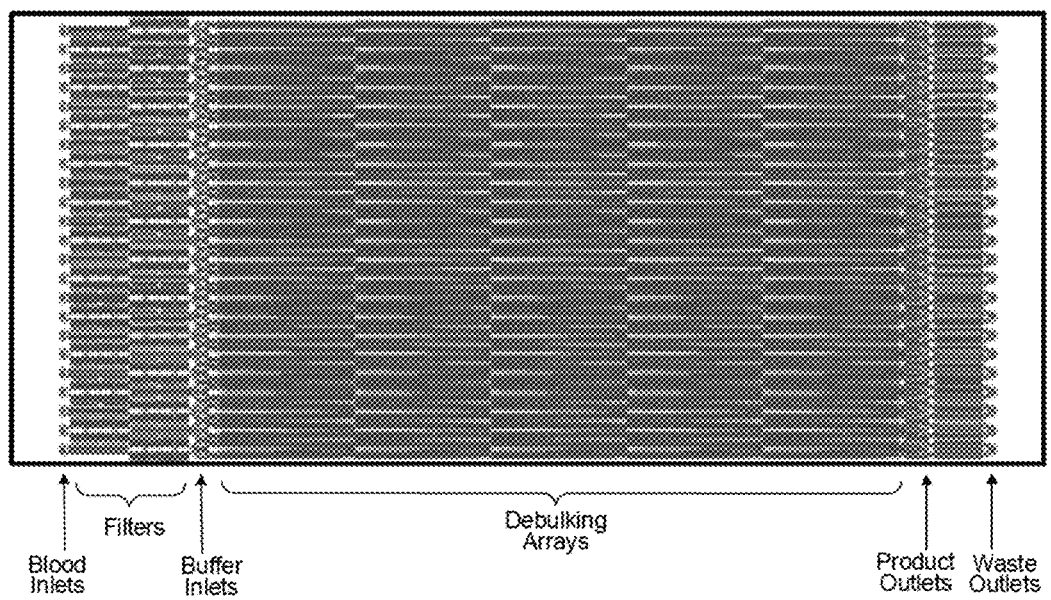
FIG. 13 is a photograph of a microscope slide that accommodates a multiplexed array of fluid shifting devices.

FIG. 12 is a plot that shows the dependence of WBC yield on fluid shift. From 2.5% shift to 3.2% shift, the yield drops from 96% to 93%. Beyond 3.2% shift, the drop in yield steepens, falling to 71% at 4.0% shift. This indicates that for the smaller shifts tested, the migration of WBCs due to inertial lift forces is large enough for essentially all of the WBCs to escape the fluid that shifts between islands. However, for the larger shifts, some WBCs, presumably the smaller WBCs, are unable to escape the fluid that shifts between islands and thereby end up in the waste Multiplexed Devices In some implementations, island arrays, such as those described herein, can be multiplexed to create very high throughput devices because the footprint of each array is small. FIG. 13 is an image of a standard microscope slide (25 mm×75 mm) that accommodates 46 arrays operating in parallel and arranged as 23 duplexes. The multiplexed array enables a combined blood sample throughput of up to ~1.4 mL/min.

OTHER EMBODIMENTS

It is to be understood that while the invention has been described in conjunction with the detailed description thereof, the foregoing description is intended to illustrate and not limit the scope of the invention, which is defined by the scope of the appended claims.

What is claimed is:

1. A method of producing a sample enriched in particles of a first type, the method comprising:
   obtaining a fluid sample comprising particles of the first type;
   altering a size of the particles of the first type in the fluid sample to provide particles of the first type having an increased effective size in the fluid sample; and
   flowing the fluid sample containing the particles of the first type having the increased effective size into a particle sorting region of a microfluidic device comprising
      a first outer wall of the particle sorting region;
      a second outer wall of the particle sorting region;
      a first microfluidic channel extending longitudinally along the particle sorting region between the first outer wall and the second outer wall;
      a second microfluidic channel extending longitudinally between the first microfluidic channel and the first outer wall;
      a first array of islands separating the first microfluidic channel from the second microfluidic channel, wherein each island in the first array is separated from an adjacent island in the first array by an opening that fluidly couples the first microfluidic channel to the second microfluidic channel;
      a third microfluidic channel extending longitudinally between the first microfluidic channel and the second outer wall;
      a second array of islands separating the first microfluidic channel from the third microfluidic channel, wherein each island in the second array is separated from an adjacent island in the second array by an opening that fluidly couples the first microfluidic channel to the third microfluidic channel;
      wherein, over a length of the particle sorting region that includes a plurality of islands from the first array and from the second array, a distance from the first outer wall to the first array of islands increases so that a fluidic resistance of the second microfluidic channel decreases along a longitudinal direction of the particle sorting region relative to the fluidic resistance of the first microfluidic channel, such that a portion of fluid from the fluid sample in the first microfluidic channel passes through the first array into the second microfluidic channel, and wherein, over the length of the particle sorting region that includes the plurality of islands from the first array and from the second array, a distance from the second outer wall to the second array of islands decreases so that a fluidic resistance of the third microfluidic channel increases along the longitudinal direction of the particle sorting region relative to the fluidic resistance of the first microfluidic channel, such that a portion of fluid from the fluid sample in the third microfluidic channel passes through the second array into the first microfluidic channel.

2. The method of claim 1, wherein inertial lift forces cause the particles of the first type having the increased effective size to remain within the first microfluidic channel.

3. The method of claim 1, wherein altering the size of the particles of the first type comprises binding the particles of the first type to one or more other particles.

4. The method of claim 3, wherein the one or more other particles comprise beads.

5. The method of claim 1, wherein altering the size of the particles of the first type comprises binding the particles of the first type to one or more other particles of a second type that is different from the first type.

6. The method of claim 1, wherein the particles of the first type are cells, and wherein altering the size of the particles of the first type comprises forming cell aggregates.

7. The method of claim 1, wherein the particles of the first type are cells, and wherein altering the size of the particles of the first type comprises causing osmotic swelling of the cells.

8. The method of claim 1, further comprising focusing the particles of the first type having the increased effective size along one or more streamlines within the first microfluidic channel.

9. The method of claim 2, wherein the fluid sample comprises particles of a second type having a particle size smaller than the effective size of the particles of the first type, and wherein inertial lift forces are insufficient to prevent the particles of the second type from flowing with the portion of the fluid sample passing through one or more of the openings between adjacent islands into the second microfluidic channel.

10. The method of claim 1, wherein a cross-sectional area of the first microfluidic channel between the first array of islands and the second array of islands is substantially constant along a longitudinal direction of the microfluidic device.

11. The method of claim 1, wherein the first array of islands consists of a single row of islands.

12. The method of claim 1, wherein the first array of islands comprises an array of two or more rows of islands.

13. The method of claim 1, wherein the second array of islands consists of a single row of islands.

14. The method of claim 1, wherein the second array of islands comprises array of two or more rows of islands.

* * * * *

UNITED STATES PATENT AND TRADEMARK OFFICE
CERTIFICATE OF CORRECTION

Page 1 of 1

PATENT NO. : 10,478,819 B2
APPLICATION NO. : 16/112275
DATED : November 19, 2019
INVENTOR(S) : Ravi Kapur, Kyle C. Smith and Mehmet Toner It is certified that error appears in the above-identified patent and that said Letters Patent is hereby corrected as shown below:

In the Specification

Column 1, Line 16, insert -- STATEMENT OF FEDERALLY SPONSORED RESEARCH
This invention was made with government support under Grant Nos. EB002503, and EB012493 awarded by the National Institutes of Health. The government has certain rights in the invention. --

Signed and Sealed this
Twenty-third Day of May, 2023

Katherine Kelly Vidal
*Director of the United States Patent and Trademark Office*